(12) United States Patent
McIntyre et al.

(10) Patent No.: US 7,413,728 B2
(45) Date of Patent: Aug. 19, 2008

(54) IMMUNE MODULATOR

(75) Inventors: Graham McIntyre, West Wickham (GB); John Lawson Stanford, Near Tonbridge (GB); Cynthia Ann Stanford, Near Tonbridge (GB); Oscar Adelmo Bottasso, Provincia de Santa Fee (AR)

(73) Assignee: UCL Biomedica PLC, London (GB)

( * ) Notice: Subject to any disclaimer, the term of this patent is extended or adjusted under 35 U.S.C. 154(b) by 86 days.

(21) Appl. No.: 10/577,907

(22) PCT Filed: Nov. 12, 2004

(86) PCT No.: PCT/GB2004/004783

§ 371 (c)(1),
(2), (4) Date: Nov. 20, 2006

(87) PCT Pub. No.: WO2005/049056

PCT Pub. Date: Jun. 2, 2005

(65) Prior Publication Data

US 2007/0104735 A1    May 10, 2007

(30) Foreign Application Priority Data

Nov. 14, 2003    (GB) ............................ 0326620.2
Feb. 24, 2004    (GB) ............................ 0404102.6

(51) Int. Cl.
A61K 49/00    (2006.01)
A61K 39/00    (2006.01)
A61K 39/02    (2006.01)
A61K 45/00    (2006.01)
A01N 63/00    (2006.01)

(52) U.S. Cl. .................. 424/9.2; 424/9.1; 424/93.1; 424/93.4; 424/184.1; 424/234.1; 424/278.1; 424/282.1; 435/243; 435/252.1; 435/253.2

(58) Field of Classification Search .......... 424/9.1, 424/9.2, 184.1, 234.1, 278.1, 282.1, 93.1, 424/93.4; 435/243, 252.1, 253.2
See application file for complete search history.

(56) References Cited

U.S. PATENT DOCUMENTS 4,599,310 A * 7/1986 Matson et al. .......... 435/71.3

FOREIGN PATENT DOCUMENTS

| AU | 706122 | 6/1999 |
| WO | WO 85/05034 | 11/1985 |
| WO | WO 03/049752 | 6/2003 |
| WO | WO 2004/022093 | 3/2004 |

OTHER PUBLICATIONS

Kunkel, H.G., "Part V, Immune Disease", in, Cecil Textbook of Medicine, eds. Beeson, McDermott, & Whyngaarden, 15th edition, W.B. Saunders Company, Phila., PA, 1979pp. 126-163.*

Conforti, Anita, et al., "Specific and long lasting suppression of rat adjuvant arthritis by low-dose *Mycobacterium butyricum*," European Journal of Pharmacology, vol. 324 No. 2-3 (1997) pp. 241-247.

Zuany-Amorim et al., "Long-Term Protective and Antigen-Specific Effect of Heat-Killed *Mycobacterium vaccae* in a Murine Model of Allergic Pulmonary Inflammation," *The Journal of Immunology*, 169: 1492-1499 (2002).

Stansby et al., "Prevention of Experimental Myointimal Hyperplasia by Immunomodulation," *Eur. J. Vasc. Endovasc. Surg.*, 23:23-28 (2002).

Haanen et al., "Selection of a Human T Helper Type 1-like T cell Subset by Mycobateria," *J. Exp. Med.*, 174: 583-592 (1991).

Stanford et al., "Immunotherapy with Mycobacterium Vaccae in the Treatment of Tuberculosis," *Frontiers in Bioscience*, 9: 1701-1719 (2004).

Smit et al., "Therapeutic treatment with heat-killed *Mycobacterium vaccae* (SRL172) in a mild and severe mouse model for allergic asthma," *European Journal of Pharmacology*, 470: 193-199 (2003).

* cited by examiner

*Primary Examiner*—Rodney P. Swartz
(74) *Attorney, Agent, or Firm*—Steptoe & Johnson LLP

(57) ABSTRACT

Use of an immune modulator composition and/or pharmaceutical composition comprising a whole cell of a bacterium from the genera *Rhodococcus*, *Gordonia*, *Nocardia*, *Dietzia*, *Tsukamurella* and *Nocardioides*, for use in the manufacture of a medicament for the treatment of an autoimmune disease or autoimmune disorder, including certain vascular disorders.

10 Claims, 12 Drawing Sheets

IMMUNE MODULATOR

FIELD OF THE INVENTION

The present invention relates to immune modulators, in particular vaccines that modulate a cellular immune response and uses thereof. The present invention relates to the use of immune modulators in the manufacture of a medicament for the treatment and/or prevention of an autoimmune disease or autoimmune disorder, including certain vascular disorders.

BACKGROUND TO THE INVENTION

The immune system is a complicated network of cells and cell components (molecules) that normally work to defend the body and eliminate infections caused by bacteria, viruses, and other invading foreign bodies. If a person has an autoimmune disease, the immune system mistakenly attacks self, targeting the cells, tissues and organs of a person's own body. A collection of immune system cells and molecules at a target site may be broadly referred to as inflammation.

There are many different autoimmune diseases, and they can each affect the body in different ways. Many of the autoimmune diseases are rare. As a group, however, autoimmune diseases afflict millions of people.

Some autoimmune diseases are known to begin or worsen with certain triggers such as viral, parasitic and chronic bacterial infections. Other less understood influences affect the immune system and the course of autoimmune diseases include ageing, chronic stress, hormones and pregnancy.

Autoimmune diseases are often chronic, requiring lifelong care and monitoring, even when the person may look or feel well. Currently, few autoimmune diseases can be cured or made to go into remission with treatment.

Physicians most often help patients manage the consequences of inflammation caused by the autoimmune disease. In some people, a limited number of immuno-suppressive medications may result in disease remission. However, even if their disease goes into remission, patients are rarely able to discontinue medication. The long-term side effects of immunosuppressive medication can be substantial.

Initiation and progression of vascular injury is a complex, multi-factorial process, but there is growing evidence that inflammatory responses play a key role. Vascular injury is involved in the development of atherosclerosis, and in thrombotic processes that lead to acute ischaemic syndromes such as myocardial infarction, stroke and peripheral artery occlusion.

Immune mechanisms may be important in the development and maintenance of atherosclerosis and myointimal hyperplasia (MIH).

Myointimal Hyperplasia (MIH) can be considered as an exaggerated healing response to injury such as balloon angioplasty. A cascade of events results in: loss of the basement membrane, migration of vascular smooth muscle cells (VSMC) from the media into the intima, VSMC proliferation and phenotypic change to a more secretory fibroblastic cell type and increased production of extracellular matrix, which eventually leads to stenosis or occlusion of the vessel. It occurs after bypass grafting and balloon angioplasty and affects approximately 30% of such cases in clinical practice. It is the major cause of failure of such procedures and treatment of the resulting stenosed and blocked vessels/grafts is problematic. The underlying cellular mechanisms leading to MIH are not well understood and to date no therapy had been developed which can effectively prevent it. The clinical relevance of the current patent relates to the very large numbers of coronary artery angioplasties which are performed annually in the UK and world-wide. Although drug eluting stents are currently producing promising results they are unlikely to prevent restenosis completely. Any safe, relatively inexpensive adjunctive therapy, such as the immunotherapy proposed in this patent, would have a major clinical impact.

The mechanisms involved in immunotherapy against restenosis are complex and not completely elucidated The endothelial injury caused by angioplasty may be exacerbated by the host immune response to hsp's. Hsp's are proteins produced by stressed cells which have been implicated in the pathogenesis and the pathophysiology of various immunological disorders including atherosclerosis (Xu Q et al. *Arterioscler Thromb* 1992; 12: 789-799). It is likely that they will be present on endothelial and smooth muscle cells in the region of an angioplasty. In effect the hsp acts as an autoantigen which can then be attacked by the immune system. This situation can be induced experimentally by immunizing with a cross-reactive mycobacterial hsp (hsp65) which leads to endothelial damage in rabbits and mice (Xu Q, et al. *Arterioscler Thromb* 1992; 12: 789-799 and George J, et al. *Circ. Res.* 2000; 86: 1203-1210). The effect appears to be dependent on IL-4 secreted by Th2 lymphocytes, and is probably mediated by antibody (George J, et al. *Circ. Res.* 2000; 86: 1203-1210 and Schett G, et al. *J. Clin. Invest.* 1995; 96: 2569-2577). The relevance of these observations to man is suggested by the ability of affinity-purified human antibody eluted from hsp65 columns to damage stressed human endothelial cells in vitro. This finding suggests that the antibody cross-reacts with hsp60 which is the human homologue of hsp65, and may be accessible to antibody when expressed on the membranes of stressed endothelial cells. It has been suggested that such antibodies binding to stressed endothelial cells may be a factor in producing coronary artery disease after heart transplantation (Crisp S J et al. *J Heart Lung Transplant* 1994; 81-91). Mukherjee et al (*Thromb Haemost* 1996; 75: 258-60) showed no association between preoperative antibody levels to hsp65 and coronary restenosis, but did show that those patients where levels of such antibodies dropped after angioplasty were less likely to restenose. In fact the role of antibodies to hsp could be complex, because patients with vascular disease have not only raised antibody, but also raised levels of the hsp themselves (Wright B H, et al *Heart Vessels* 2000; 15: 18-22). Thus an apparent fall in antibody levels may merely reflect an increase in levels of the protein. Moreover the hsp have regulatory effects, and bind to arterial smooth muscle cells, leading to enhanced survival without a requirement for internalization (Johnson A D et al. *Atherosclerosis* 1990; 84: 111-119).

SUMMARY OF THE INVENTION

The present invention is predicated upon the surprising finding that a whole cell of a bacterium from any one of the actinomycete genera *Rhodococcus, Gordonia, Nocardia, Dietzia, Tsukamurella* and *Nocardioides* administered to a test subject can elicit a modification of the immune system, in particular the cellular immune system of that test subject, which effects a preventative and/or therapeutic effect on autoimmune diseases or autoimmune disorders, particularly those which involve the inflammation of the intima of blood vessels for example.

An advantage of the use of compositions comprising a whole cell of a bacterium from any one of the actinomycete genera *Rhodococcus, Gordonia, Nocardia, Dietzia, Tsukamurella* and *Nocardioides* to effectively treat and/or prevent autoimmune diseases and autoimmune disorders, particularly those which involve the inflammation of the intima of blood vessels for example, may be that this treatment and/or prevention is effected whilst producing fewer long-term side effects than the chemotherapies, i.e. the immunosuppressive medication, now routinely used.

The phrase "cellular immune system", as used herein, includes a cell-mediated immune response which depends upon the presence of T lymphocytes. The term "T lymphocytes" includes cytotoxic T lymphocytes, helper T cells, suppresser T cells and regulatory T cells. Modification of a cell-mediated immune response may be used, for example, to overcome cell-mediated immune disorders including, for example autoimmune diseases or disorders.

The terms "modulate", "modify", "modification" and other derivatives thereof, as used herein, mean downregulating, inhibiting, inducing, stimulating, upregulating, altering or otherwise affecting a component or components of the cellular immune system.

DETAILED ASPECTS OF THE PRESENT INVENTION

The present invention further provides the use of an immune modulator composition or a pharmaceutical composition comprising a whole cell of a bacterium from one or more of the genera *Rhodococcus, Gordonia, Nocardia, Dietzia, Tsukamurella* and *Nocardioides*, in the manufacture of a medicament for the treatment or prevention of an autoimmune disease or an autoimmune disorder.

Suitably, the autoimmune disease or autoimmune disorder is of the type where the subjects own immune system damages one or more of the subjects tissues. Suitably, the autoimmune response may be triggered by something within the subject or something within the subject's environment.

Suitably the autoimmune disease or autoimmune disorder according to the present invention may be one which follows an initiating cause. For example, the autoimmune disease or autoimmune disorder according to the present invention may be one which is caused by an infection and/or some other initiating cause. Potential initiating causes may be, by way of example, old age, infection (for example parasitic infection), treatment with steroids, repeated vaccination with alum, pregnancy and/or cancers.

The present invention further provides the use of an immune modulator composition or a pharmaceutical composition comprising a whole cell of a bacterium from one or more of the genera *Rhodococcus, Gordonia, Nocardia, Dietzia, Tsukamurella* and *Nocardioides*, in the manufacture of a medicament for the treatment or prevention of an autoimmune disease, wherein the autoimmune disease or autoimmune disorder involves inflammation of the intima of a blood vessel.

Suitably, the autoimmune disease or autoimmune disorder according to the present invention may, as well as involving inflammation of the intima of a blood vessel, involve inflammation of the muscular layer of a blood vessel or of the myocardium.

Suitably, the autoimmune disease or autoimmune disorder according to the present invention may be one which is preceded by or caused by a vascular disorder.

The autoimmune disease or autoimmune disorder according to the present invention maybe one or more of the following: arthritis, particularly rheumatoid arthritis, psoriasis, psoriatic arthropathy, scleroderma, thyroiditis, post-transplant intimal hyperplasia, graft rejection and vascular disorders.

Suitably, the vascular disorders according to the present invention may include any vascular disease or disorder which comprises an autoimmune element, for example one which is caused by an autoimmune response.

Suitably, vascular disorders according to the present invention may include one or more of Raynaud's disease and phenomenon, anterior uveitis, obliterative vascular disorder, atheroma formation (otherwise known as arteriosclerosis), arteritis, myointimal hyperplasia (natural or following angioplasty), inflammatory and autoimmune thickening of the intima and/or muscular layer of blood vessels, inflammatory blood vessel lesions, atherosclerotic heart disease, reperfusion injury, cardiac conduction disturbances, myocarditis, myocardial infarction.

Suitably, the graft rejection according to the present invention may be chronic graft rejection, particularly in the absence of an immunosuppressant. Thus, the composition according to the present invention may be used as a replacement for the conventional immunosuppressant administered prior to, during and/or after transplantation. The compositions according to the present invention may be used when transplanting natural or artificial cells, tissues and organs, such as one or more of the following: corneas, bone marrow, organs (e.g. kidney, liver), lenses, pacemakers, natural or artificial skin tissue, islet cells.

The present invention further provides the use of an immune modulator composition or a pharmaceutical composition comprising a whole cell of a bacterium from one or more of the genera *Rhodococcus, Gordonia, Nocardia, Dietzia, Tsukamurella* and *Nocardioides*, in the manufacture of a medicament for the treatment or prevention of a vascular disorder.

The present invention further provides the use of an immune modulator composition or a pharmaceutical composition comprising a whole cell of a bacterium from one or more of the genera *Rhodococcus, Gordonia, Nocardia, Dietzia, Tsukamurella* and *Nocardioides*, in the manufacture of a medicament for the treatment or prevention of arthritis, particularly rheumatoid arthritis.

The present invention further provides the use of an immune modulator composition or a pharmaceutical composition comprising a whole cell of a bacterium from one or more of the genera *Rhodococcus, Gordonia, Nocardia, Dietzia, Tsukamurella* and *Nocardioides*, in the manufacture of a medicament for the treatment or prevention of graft rejection.

In a further aspect the present invention provides the use of an immune modulator composition or a pharmaceutical composition comprising a whole cell of a bacterium from one or more of the genera *Rhodococcus, Gordonia, Nocardia, Dietzia, Tsukamurella* and *Nocardioides*, in the manufacture of a medicament for the treatment or prevention of psoriasis.

The term "immune modulator", as used herein, means a substance which modulates a cellular immune system of a subject.

The term "whole cell", as used herein, means a bacterium which is intact, or substantially intact. In particular, the term "intact" as used herein means a bacterium which is comprised of all of the components present in a whole cell, particularly a whole, viable cell, and/or a bacterium which has not been specifically treated to remove one or more components from it. By the term "substantially intact" as used herein it is meant that although the isolation and/or purification process used in obtaining the bacterium may result in, for example, a slight modification to the cell and/or in the removal of one or more of the components of the cell, the degree to which such a modification and/or removal occurs is insignificant. In particular, a substantially intact cell according to the present invention has not been specifically treated to remove one or more components from it.

Although it has been suggested that individual components of bacterial cells could be used to elicit an adjuvant effect, prior to the present invention the use of whole cells of bacterium from the genera *Rhodococcus, Gordonia, Nocardia, Dietzia, Tsukamurella* and *Nocardioides* in accordance with the present invention was not contemplated. Surprisingly, it has been found that by using a whole cell of a bacterium from said genera treatment and/or prevention of an autoimmune disease or an autoimmune disorder can be effected. The modulation of a cellular immune response caused by administration of said whole cell of said bacterium may be advantageously long lasting as compared with the response elicited by administration of an individual component of the bacterium.

Preferably, the composition according to the present invention comprises more than one whole cell, and more preferably comprises a plurality of whole cells.

Suitably, the immune modulator composition according to the present invention may comprise an antigen and an adjuvant, wherein said adjuvant comprises a whole cell of a bacterium from the genera *Rhodococcus, Gordonia, Nocardia, Dietzia, Tsukamurella* and *Nocardioides*. The said antigens may be those shared by these genera with other microorganisms and the mitochondria of eukaryotic, for example vertebrate, cells.

In another aspect, the immune modulator composition may be a pharmaceutical composition comprising a whole cell of a bacterium from the genera *Rhodococcus, Gordonia, Nocardia, Dietzia, Tsukamurella* and *Nocardioides* and optionally a pharmaceutically acceptable carrier, diluent or excipient, which immune modulator composition in use modifies a cellular immune response.

In a further aspect, the immune modulator composition and/or a pharmaceutical composition may comprise a whole cell of a bacterium from the genera *Rhodococcus, Gordonia, Nocardia, Dietzia, Tsukamurella* and *Nocardioides*, and at least one added cytokine, such as interleukin 2 for example. The cytokine may help to reinforce the immune modulatory action of the present invention.

Suitably, the antigen or antigenic determinant may be an antigen or antigenic determinant from one or more of the following: BCG (bacillus of Calmette and Guerin) vaccine, diphtheria toxoid vaccine, diphtheria/tetanus/pertussis (DTP or Triple) vaccine, pertussis vaccine, tetanus toxoid vaccine, measles vaccine, mumps vaccine, rubella vaccine, OPV (oral poliomyelitis vaccine) and *Mycobacterium vaccae*, or part thereof (as taught in GB0025694.1). This list is in no way limiting and suitable antigens from other sources may be added to the compositions according to the present invention so that responses to those antigens may also benefit from the induced regulation of response resulting from administering the composition according to the present invention. Other suitable antigens may be antigens from other viruses, tumours, parasites or other bacteria not naturally present in the modulator composition according to the present invention.

Suitably, the immune modulator composition and/or pharmaceutical composition may comprise two or more such antigens or antigenic determinants.

In a further aspect, the immune modulator composition or pharmaceutical composition comprising a whole cell of a bacterium from the genera *Rhodococcus, Gordonia, Nocardia, Dietzia, Tsukamurella* and *Nocardioides* according to the present invention may be used in or as a vaccine.

Suitably, the vaccine may be a prophylactic vaccine or a therapeutic vaccine.

In a further aspect, the present invention provides an immune modulator composition or a pharmaceutical composition comprising a whole cell of a bacterium from the genera *Rhodococcus, Gordonia, Nocardia, Dietzia, Tsukamurella* and *Nocardioides* for use in the treatment or prevention of an autoimmune disease or an autoimmune disorder In one aspect, the whole cell of the bacterium according to the present invention may downregulate a Th2 response.

In another aspect, the whole cell of the bacterium according to the present invention may upregulate a Th1 response.

Suitably, the whole cell of the bacterium according to the present invention may downregulate a Th2 response and upregulate a Th1 response.

Alternatively, the whole cell of the bacterium according to the present invention may upregulate a Th1 response whilst not affecting a Th2 response.

Alternatively, the whole cell of the bacterium according to the present invention may downregulate a Th2 response, whilst also downregulating a Th1 response.

Alternatively, the whole cell of the bacterium according to the present invention may upregulate a Th2 response, whilst also upregulating a Th1 response.

In another aspect, the present invention provides a method for treating or preventing an autoimmune disease or an autoimmune disorder comprising administering an effective amount of a pharmaceutical composition and/or immune modulator composition comprising a whole cell of a bacterium from one or more of the genera *Rhodococcus, Gordonia, Nocardia, Dietzia, Tsukamurella* and *Nocardioides* to a subject wherein the said composition modulates a cellular immune response.

Suitably the effective amount of the pharmaceutical composition and/or immune modulator composition may be administered as a single dose. Alternatively, the effective amount of the pharmaceutical composition and/or immune modulator composition may be administered in multiple (repeat) doses, for example two or more, three or more, four or more, five or more, ten or more, or twenty or more repeat doses.

In particular, such repeated doses may be needed for the treatment of established and chronic conditions, for example.

In a further aspect of the present invention, there is provided a method for protecting, including immunizing, a subject against an autoimmune disease or an autoimmune disorder comprising administering a pharmaceutical composition and/or immune modulator composition comprising a whole cell of a bacterium from the genera *Rhodococcus, Gordonia, Nocardia, Dietzia,* and *Nocardioides*.

The term "protected" as used herein means that the subject is less susceptible to the disease/disorder as compared with a subject not treated or administered with the compositions according to the present invention and/or that the subject is more able to counter or overcome the disease/disorder as compared with a subject not treated or administered with the compositions according to the present invention.

In another aspect, the present invention provides administering an effective amount of a pharmaceutical composition and/or an immune modulator composition according to the present invention to a subject, wherein said composition is co-administered with an antigen or antigenic determinant.

When the composition is co-administered with an antigen or antigenic determinant in accordance with the present invention the antigen or antigenic determinant may suitably be an antigen or antigenic determinant from one or more of the following: BCG (bacillus of Calmette and Guerin) vaccine, diphtheria toxoid vaccine, diphtheria/tetanus/pertussis (DTP or Triple) vaccine, pertussis vaccine, tetanus toxoid vaccine, measles vaccine, mumps vaccine, rubella vaccine, OPV (oral poliomyelitis vaccine) and *Mycobacterium vaccae*, or part thereof (as taught in GB0025694.1). Suitably two or more, or three or more, of such antigens or antigenic determinants may be co-administered with a pharmaceutical composition or an immune modulator composition according to the present invention.

Preferably, a medicament according to the present invention is used for the treatment or prevention of an autoimmune disease or an autoimmune disorder.

In a further aspect of the present invention, the pharmaceutical composition or the immune modulator composition according to the present invention may comprise bacteria from more than one of the genera *Rhodococcus, Gordonia, Nocardia, Dietzia, Tsukamurella* and *Nocardioides*. Suitably, the composition may comprise two or more, or three or more, bacteria from any one of the genera *Rhodococcus, Gordonia, Nocardia, Dietzia, Tsukamurella* and *Nocardioides*.

Preferably, the bacteria for use in accordance with the present invention are from the genera *Rhodococcus, Gordonia, Nocardia, Dietzia, Tsukamurella* and *Nocardioides*, including any species from any of these genera such as *Gordonia bronchialis, G. amarae, G. sputi, G. terrae, Nocardia asteroides, Dietzia maris, Tsukamurella paurometabola, Rhodococcus ruber, Rhodococcus rhodnii, R. coprophilus, Nocardioides albus* and *Tsukamurella inchonensis* for example. Suitably, the species used from each particular genus are ones which can be grown on medium, which is a low, preferably non-, antigenic medium. By way of example only, a suitable non-antigenic medium is Sauton's medium.

Suitably, the bacteria for use in accordance with the present invention may be from the genus *Rhodococcus*. including *Rhodococcus ruber* (previously known as *Nocardia rubra*), *Rhodococcus rhodocrous, Rhodococcus rhodnii, Rhodococcus coprophilus, Rhodococcus opacus, Rhodococcus erythopolis*.

Suitably, the bacteria for use in accordance with the present invention may be *Rhodococcus ruber*.

Preferably, the bacterium according to the present invention is killed prior to use. Suitably, the bacterium according to the present invention may be killed by heat-treatment thereof, for example, heat-treatment in an autoclave at 121° C. for 15 minutes.

Other suitable treatments for killing the bacterium may include ultraviolet or ionizing radiation or treatment with chemicals such as phenol, alcohol or formalin.

Suitably, the bacterium according to the present invention may be purified and/or isolated.

Suitably, the bacterium according to the present invention may be suspended in water or buffered saline, suitably borate buffered at pH 8.

The term "subject", as used herein, means an animal. Suitably, the subject may be for example any animal, including birds, crustaceans (such as shrimps for example), fish and mammals. Preferably, the subject is a mammal, including for example livestock and humans. In some aspects of the present invention, the subject may suitably be a human.

When the pharmaceutical composition or immune modulator composition is administered (for the first time if more than one administration is to be made) to livestock, preferably it is administered after the livestock has suckled for the first time. In particular, for some applications it may be important to allow the infant to take in and/or digest the parents colostrum prior to administering the first (where there is more than one dose) or only dose of the pharmaceutical composition or immune modulator composition. For the avoidance of doubt, for some applications the first administration of the pharmaceutical composition or immune modulator composition should be given between about 1-4 days post-birth, preferably 1-3 days post-birth, more preferably 1-2 days post-birth, preferably 2-3 days post-birth. Subsequent administrations may be given 7 days and/or 8-12 weeks after the first injection.

The term "immune modulator" as used herein includes a vaccine.

Preferably the bacterium is a bacterium from the order Actinomycetales. However, preferably the bacterium is not *Mycobacterium vaccae*. In one embodiment, preferably the bacterium is not from the genus *Mycobacterium*.

Therapeutic Uses

The immune modulators of the present invention may be used in therapy. In particular such compounds may be used to modulate T lymphocyte responses in vivo and/or other cells involved in an immune response in vivo.

Immune modulator/pharmaceutical compositions capable of modulating, in particular blocking, T cell proliferation and/or differentiation and/or activity may be used against any disorder which is susceptible to prevention or treatment by the modulation of an adaptive immune response, i.e. a cellular immune response.

Suitably, the autoimmune disease or autoimmune disorder according to the present invention is of the type where the subjects own immune system damages one or more of the subjects tissues. Suitably, the autoimmune response may be triggered by something within the subject or something within the subject's environment.

Suitably the autoimmune disease or autoimmune disorder according to the present invention may be one which follows an initiating cause. For example, the autoimmune disease or autoimmune disorder according to the present invention may be one which is caused by an infection and/or some other initiating cause. Potential initiating causes may be, by way of example, old age, infection (for example parasitic infection), treatment with steroids, repeated vaccination with alum, pregnancy and/or cancers.

Suitably, the autoimmune disease or autoimmune disorder according to the present invention may be one which involves inflammation of the intima of a blood vessel.

Suitably, the autoimmune disease or autoimmune disorder according to the present invention may, as well as involving inflammation of the intima of a blood vessel, involve inflammation of the muscular layer of a blood vessel or of the myocardium.

Suitably, the autoimmune disease or autoimmune disorder according to the present invention may be one which is preceded by or caused by a vascular disorder.

The autoimmune disease or autoimmune disorder according to the present invention may be one or more of the following: arthritis, particularly rheumatoid arthritis, psoriasis, psoriatic arthropathy, scleroderma, thyroiditis, post-transplant intimal hyperplasia, graft rejection and vascular disorders.

Suitably, the vascular disorders according to the present invention may include any vascular disease or disorder which comprises an autoimmune element, for example one which is caused by an autoimmune response.

Suitably, vascular disorders according to the present invention may include one or more of Raynaud's disease and phenomenon, anterior uveitis, obliterative vascular disorder, atheroma formation (otherwise known as arteriosclerosis), arteritis, myointimal hyperplasia (natural or following angioplasty), inflammatory and autoimmune thickening of the intima and/or muscular layer of blood vessels, inflammatory blood vessel lesions, atherosclerotic heart disease, reperfusion injury, cardiac conduction disturbances, myocarditis and myocardial infarction.

Suitably, the graft rejection according to the present invention may be chronic graft rejection, particularly in the absence of an immunosuppressant. Thus, the composition according to the present invention may be used as a replacement to the conventional immunosuppressant administered prior to, during and/or after transplantation. The compositions according to the present invention may be used when transplanting natural or artificial cells, tissues and organs, such as one or more of the following: corneas, bone marrow, organs (e.g. kidney, liver), lenses, pacemakers, natural or artificial skin tissue, islet cells.

T Helper Cells

The term 'Th1' as used herein refers to a type 1 T-helper cell (Th1). The term may also be used herein to refer to the response mediated by or through such a cell type. Such a response may include one or more of the secretion of Interleukin-2 (IL-2), the secretion of Interferon-gamma (IFN-γ), activation of macrophages, activation of cytotoxic T-cells, or any other Th1-associated event. Thus, the term 'Th1' may include Th1 cell(s) as well as the immune response(s) which such cell(s) produce.

The term 'Th2' as used herein refers to a type 2 T-helper cell (Th2). The term may also be used herein to refer to the response mediated by or through such a cell type. Such a response may include one or more of the secretion of Interleukin-4 (IL-4), the secretion of the splice variant interleukin IL-4δ2, the secretion of Interleukin-5 (IL-5), increase in levels of cell determinant 30 (CD30) on lymphocytes, increase in levels of Immunoglobulin-E (IgE) in the blood or eosinophils in the blood, or any other Th2-associated event. Thus, the term 'Th2' may include Th2 cell(s) as well as the immune response(s) which such cell(s) produce.

It is known that various conditions may result in or from an unregulated or inappropriately regulated cellular immune response, in particular in the activation and/or proliferation of Th1 and/or Th2, which if left unregulated or inappropriately regulated has been found to result in one or more detrimental effects on the subject.

An unregulated or inappropriately regulated cellular immune response has also been observed in autoimmune disorders such as for example inflammatory vascular diseases such as arteriosclerosis, myointimal hyperplasia following angioplasty and anterior uveitis, and during graft transplantation/rejection. By way of further example, Stansby et al. *Eur J Vasc Endovasc Surg* 2002; 23: 23-28 tested the hypothesis that treatment with a mycobacterial preparation that modulates the antibody response, would diminish vascular disease, i.e. restenosis in a rat angioplasty model. It was shown that immunomodulation with mycobacterial material suitable for use in man, can reduce MIH. Since such modulation has low risk, this raises the prospect of an important new therapeutic modality to combat restenosis.

Accordingly, an aim of the present invention is to promote and establish the regulation of a cellular immune response, including the regulation or modulation of Th1 and/or Th2, in such a way so as to overcome the negative effects of the unregulated or inappropriately regulated cellular immune response.

Suitably, the use of an immune modulator composition and/or pharmaceutical composition according to the present invention modulates the Th1 or Th2 response, i.e. a Th1 or Th2 response that results in, for example, tissue damage.

Suitably, the use of an immune modulator composition and/or pharmaceutical composition according to the present invention may decrease the Th1 response and decrease the Th2 response.

Suitably, the use of an immune modulator composition and/or pharmaceutical composition according to the present invention may increase the Th1 response without affecting the Th2 response.

Suitably, the use of an immune modulator composition and/or pharmaceutical composition according to the present invention may increase the Th1 response and decrease the Th2 response.

Suitably, the use of an immune modulator composition and/or pharmaceutical composition according to the present invention may increase the Th1 response and increase the Th2 response.

Suitably, a skilled person can test a specific species of each genus according to the present invention to determine its specific Th1/Th2 response.

An unregulated or inappropriately regulated immune response may play a role in the establishment of disease due to the fact that some diseases cause, or are a consequence of, shifted Th1 and/or Th2 responses. Accompanying these atypical Th1 and Th2 reactions are a series of abnormal inflammatory responses, which may take part in the mechanisms underlying tissue pathology.

By way of example only, the immune modulator composition and/or pharmaceutical composition according to the present invention may counteract an autoimmune disease or autoimmune disorder.

Vaccines

The preparation of vaccines which contain one or more substances as an active ingredient(s), is known to one skilled in the art. Typically, such vaccines are prepared as injectables, either as liquid solutions or suspensions; solid forms suitable for solution in, or suspension in, liquid prior to injection may also be prepared. The preparation may also be emulsified, or the active ingredient(s) encapsulated in liposomes. The active ingredients are often mixed with excipients which are pharmaceutically acceptable and compatible with the active ingredient. Suitable excipients are, for example, water, saline, dextrose, glycerol, ethanol, or the like and combinations thereof. Alternatively, the vaccine may be prepared, for example, to be orally ingested and/or capable of inhalation.

In addition, if desired, the vaccine may contain minor amounts of auxiliary substances such as wetting or emulsifying agents and pH buffering agents.

Administration

Typically, a physician will determine the actual dosage of a vaccine, immune modulator composition and pharmaceutical composition which will be most suitable for an individual subject and it will vary with the age, weight and response of the particular patient. The dosages below are exemplary of the average case. There can, of course, be individual instances where higher or lower dosage ranges are merited.

Preferably, the actual dosage that is used results in minimal toxicity to the subject.

The compositions of the present invention may be administered by direct injection. The composition may be formulated for parenteral, mucosal, intramuscular, intravenous, subcutaneous, intraocular, intradermal or transdermal administration.

Suitably, the composition according to the present invention may be administered at a dose of 1 nanogram to 100 milligrams organisms, preferably 10 nanograms to 10 milligrams organisms, more preferably 100 nanograms to 5 milligrams organisms, and even more preferably 100 nanograms to 1 milligram organisms. Typically, the composition according to the present invention may be administered at a dose of 100 micrograms to 1 milligram bacteria for human and animal use.

If the compositions of the present invention are to be administrated as immune enhancers, then 1 nanogram to 100 milligrams organisms per dose, preferably 10 nanograms to 10 milligrams organisms per dose, more preferably 100 nanograms to 5 milligrams organisms per dose, and even more preferably 100 nanograms to 1 milligram organisms per dose, and even more preferably, 100 micrograms to 1 milligram bacteria per dose for human and animal use may be administered at regular intervals.

As will be readily appreciated by a skilled person the dosage administered will be dependent upon the organism to which the dose is being administered.

The term "administered" includes delivery by delivery mechanisms including injection, lipid mediated transfection, liposomes, immunoliposomes, lipofectin, cationic facial amphiphiles (CFAs) and combinations thereof, or even viral delivery. The routes for such delivery mechanisms include but are not limited to mucosal, nasal, oral, parenteral, gastrointestinal, topical, or sublingual routes.

The term "administered" includes but is not limited to delivery by a mucosal route, for example, as a nasal spray or aerosol for inhalation or as an ingestable solution, capsule or tablet; a parental route where delivery is by an injectable form, such as, for example, an intravenous, intramuscular, intradermal or subcutaneous route.

The term "co-administered" means that the site and time of administration of each of the adjuvants(s), antigen(s) and/or antigenic determinant(s) of the present invention are such that the necessary modulation of the immune system is achieved. Thus, whilst the antigen(s) and adjuvant(s) may be administered at the same moment in time and at the same site, there may be advantages in administering the antigen(s) and/or antigenic determinant(s) at a different time and to a different site from the adjuvant(s). The antigen(s) and/or antigenic determinant(s) and adjuvant(s) may even be delivered in the same delivery vehicle—and the antigen(s) and/or antigenic determinant(s) and adjuvant(s) may be coupled and/or uncoupled and/or genetically coupled and/or uncoupled. By way of example only, the immune modulator composition according to the present invention may be administered before, at the same time or post administration of one or more antigens or further antigens.

The antigen, antigenic determinant, peptide or homologue or mimetic thereof may be administered separately or co-administered to the host subject as a single dose or in multiple doses.

The immune modulator composition and/or pharmaceutical composition of the invention may be administered by a number of different routes such as injection (which includes parenteral, subcutaneous, intradermal and intramuscular injection) intranasal, mucosal, oral, intra-vaginal, urethral or ocular administration.

Preferably, in the present invention, administration is by injection. More preferably the injection is intradermal.

Preferably, in the present invention, administration is by an orally acceptable composition.

For vaccination the composition can be provided in 0.1 to 0.2 ml of aqueous solution, preferably buffered physiological saline, and administered parenterally, for example by intradermal inoculation. The vaccine according to the invention is preferably injected intradermally. Slight swelling and redness, sometimes also itching may be found at the injection site. The mode of administration, the dose and the number of administrations can be optimised by those skilled in the art in a known manner.

Antigens

As used herein, an "antigen" means an entity which, when introduced into an immunocompetent host, modifies the production of a specific antibody or antibodies that can combine with the entity, and/or modifies the relevant Th response, such as Th2 and/or Th1, The antigen may be a pure substance, a mixture of substances or soluble or particulate material (including cells or cell fragments or cell sonicate). In this sense, the term includes any suitable antigenic determinant, cross reacting antigen, alloantigen, xenoantigen, tolerogen, allergen, hapten, and immunogen, or parts thereof, as well as any combination thereof, and these terms are used interchangeably throughout the text.

The term "antigenic determinant or epitope" as used herein refers to a site on an antigen which is recognised by an antibody or T-cell receptor, or is responsible for evoking the T-helper cell response. Preferably it is a short peptide derived from or as part of a protein antigen. However the term is also intended to include glycopeptides and carbohydrate epitopes. The term also includes modified sequences of amino acids or carbohydrates which stimulate responses which recognise the whole organism.

A "preventative" or "prophylactic" vaccine is a vaccine which is administered to naive individuals to prevent development of a condition, such as by stimulating protective immunity.

A "therapeutic" vaccine is a vaccine which is administered to individuals with an existing condition to reduce or minimise the condition or to abrogate the immunopathological consequences of the condition.

Adjuvants

The term 'adjuvant' as used herein means an entity capable of augmenting or participating in the influencing of an immune response. An adjuvant is any substance or mixture of substances that assists, increases, downregulates, modifies or diversifies the immune response to an antigen.

The immune modulator composition and/or pharmaceutical composition according to the present invention may comprise one or more adjuvants which enhance the effectiveness of the immune modulator composition and/or pharmaceutical compositions. Examples of additional adjuvants which, may be effective include but are not limited to: aluminium hydroxide, aluminium phosphate, aluminium potassium sulphate (alum), beryllium sulphate, silica, kaolin, carbon, water-in-oil emulsions, oil-in-water emulsions, muramyl dipeptide, bacterial endotoxin, lipid X, *Corynebacterium parvum* (*Propionobacterium acnes*), *Bordetella pertussis*, *Mycobacterium vaccae*, polyribonucleotides, sodium alginate, lanolin, lysolecithin, vitamin A, interleukins such as interleukin 2 and interleukin-12, saponin, liposomes, levamisole, DEAE-dextran, blocked copolymers or other synthetic adjuvants. Such adjuvants are available commercially from various sources, for example, Merck Adjuvant 65 (Merck and Company, Inc., Rahway, N.J.) or Freund's Incomplete Adjuvant and Complete Adjuvant (Difco Laboratories, Detroit, Mich.). Only aluminium hydroxide is approved for human use. Some of the other adjuvants, such as *M. vaccae* for example, have been approved for clinical trials.

Suitably, the adjuvant may be a whole cell of a bacterium from any one of the genera *Rhodococcus, Gordonia, Nocardia, Dietzia, Tsukamurella* and *Nocardioides*.

In the art, it is known that DNA vaccines, which are essentially DNA sequences attached to gold particles and which are fired into the skin by a helium gun, are efficient vaccine delivery systems. Unlike conventional vaccines, these DNA vaccines do not require a traditional adjuvant component. In accordance with a further aspect of the present invention, the immune modulator composition as defined herein may suitably be used in conjunction with such DNA vaccines to augment or participate in the influencing of the immune response.

Pharmaceutical Compositions

The present invention also relates to a pharmaceutical composition comprising a therapeutically effective amount of a whole cell of a bacterium from the genera *Rhodococcus, Gordonia, Nocardia, Dietzia, Tsukamurella* and *Nocardioides* and optionally a pharmaceutically acceptable carrier, diluent or excipients (including combinations thereof).

The pharmaceutical composition may comprise two components—a first component comprising an antigen and a second component comprising an adjuvant thereof. The first and second component may be delivered sequentially, simultaneously or together, and even by different administration routes.

The pharmaceutical compositions may be for human or animal usage in human and veterinary medicine and will typically comprise any one or more of a pharmaceutically acceptable diluent, carrier, or excipient. Acceptable carriers or diluents for therapeutic use are well known in the pharmaceutical art, and are described, for example, in Remington's Pharmaceutical Sciences, Mack Publishing Co. (A. R. Gennaro edit. 1985). The choice of pharmaceutical carrier, excipient or diluent can be selected with regard to the intended route of administration and standard pharmaceutical practice.

The pharmaceutical compositions may comprise as—or in addition to—the carrier, excipient or diluent any suitable binder(s), lubricant(s), suspending agent(s), coating agent(s), solubilizing agent(s).

Preservatives, stabilizers, dyes and even flavouring agents may be provided in the pharmaceutical composition. Examples of preservatives include sodium benzoate, sorbic acid and esters of p-hydroxybenzoic acid. Antioxidants and suspending agents may be also used.

There may be different composition/formulation requirements dependent on the different delivery systems. By way of example, the pharmaceutical composition of the present invention may be formulated to be delivered using a minipump or by a mucosal route, for example, as a nasal spray or aerosol for inhalation or ingestable solution, or parenterally in which the composition is formulated by an injectable form, for delivery, by, for example, an intravenous, intramuscular, intradermal or subcutaneous route. Alternatively, the formulation may be designed to be delivered by both routes.

Preferably in the present invention the formulation is of injectable form. More preferably the formulation is intradermally injected.

Preferably in the present invention the formulation is an orally acceptable composition.

Where the agent is to be delivered mucosally through the gastrointestinal mucosa, it should be able to remain stable during transit through the gastrointestinal tract; for example, it should be resistant to proteolytic degradation, stable at acid pH and resistant to the detergent effects of bile.

Where appropriate, the pharmaceutical compositions can be administered by inhalation, in the form of a suppository or pessary, topically in the form of a lotion, solution, cream, ointment or dusting powder, by use of a skin patch, orally in the form of tablets containing excipients such as starch or lactose, or in capsules or ovules either alone or in admixture with excipients, or in the form of elixirs, solutions or suspensions containing flavouring or colouring agents, or they can be injected parenterally, for example intravenously, intramuscularly, intradermally or subcutaneously. For parenteral administration, the compositions may be best used in the form of a sterile aqueous solution which may contain other substances, for example enough salts or monosaccharides to make the solution isotonic with blood. For buccal or sublingual administration the compositions may be administered in the form of tablets or lozenges which can be formulated in a conventional manner.

Pharmaceutical Combinations

The agent of the present invention may be administered with one or more other pharmaceutically active substances. By way of example, the present invention covers the simultaneous, or sequential treatments with an immune modulator composition and/or pharmaceutical composition according to the present invention, and one or more steroids, analgesics, antivirals, interleukins such as IL-2, or other pharmaceutically active substance(s).

It will be understood that these regimes include the administration of the substances sequentially, simultaneously or together.

Immune Enhancer

The term "immune enhancer" as used herein means one or more bacteria either isolated or in culture which when administered to a subject benefit the health of that subject. Preferably, this benefit is achieved by the modification of the cellular immune response of the subject.

In accordance with the present invention, immune enhancers may be used, for example, for the treatment or prevention of an autoimmune disease or autoimmune disorder.

The immune enhancers may be administered by consumption in specially designed food or in animal feeds.

The immune enhancers may also be administered by other routes—such as direct injection.

Preferably, the bacteria are killed so as to avoid the difficulties of maintaining live products.

Identifying a Bacterium that Modulates a Cellular Immune Response

In another aspect, the present invention relates to a method for identifying one or more whole cells of bacteria from the genera *Rhodococcus, Gordonia, Nocardia, Dietzia, Tsukamurella* and *Nocardioides* that modulate (e.g. modify) a cellular immune response comprising the steps of: (a) contacting a first test animal with an immunostimulant; (b) contacting a second test animal with an immunostimulant mixed with a bacterium; (c) measuring the cellular immune response in each of the test animals; and (d) comparing the cellular immune response in each of the test animals, wherein, a lower cellular immune response from the immunostimulant mixed with a bacterium in comparison to the immunostimulant alone is indicative of a modification of the cellular immune response by the bacterium.

In another aspect, the present invention relates to a method of determining the Th1/Th2 response of a species of bacteria selected from the genera *Rhodococcus, Gordonia, Nocardia, Dietzia, Tsukamurella* and *Nocardioides* which method comprises utilisation of the tuberculin skin test. In mice, the tuberculin skin test is preferably carried out on the foot pad. In a predominant Th1 reaction the positive foot pad immune response is maximal at 24 hours and diminishes at 48 hours. However, as the Th2 reactivity increases then the 48 hour positive foot pad immune response increases and can even exceed the foot pad immune response at 24 hour.

The effect of BCG vaccination is well documented using this tuberculin skin test. Thus, the test assay can be used to assess whether or not the introduction of an immune modulator composition according to the present invention modulates the BCG cellular immune response.

As used herein, the term "test animal" refers to any animal that elicits a cellular immune response to the immunostimulant. Preferably, the test animal(s) is a mammal. More preferably, the test animal(s) is a rat, hamster, rabbit, guinea pig or mouse. More preferably, the test animal(s) is a mouse.

Preferably, the bacterium modifies the T helper cell response. Suitably, the bacterium may modify the T helper cell response by decreasing the Th1 and Th2 response. Suitably, the bacterium may modify the T helper cell response by increasing the Th1 response and decreasing the Th2 response. Suitably, the bacterium may modify the T helper cell response by increasing the Th1 response without affecting the Th2 response.

Preferably, the immunostimulant will have a known Th1 and Th2 response. For example, with the immunostimulant BCG the reaction is usually largest at 24 h when it is an indicator of the Th1 response; the reaction at 48 h is usually less and includes a Th2 contribution. It is known that BCG predominantly stimulates a Th1 response. By use of such immunostimulants it may be possible to determine the Th1/Th2 response of a test bacterium and, thus, it may be possible to identify one or more bacteria which have a desired Th1/Th2 response to treat and/or prevent a particular disease and/or disorder.

Preferably, the cellular immune response is measured using the tuberculin skin test. Vaccination with an immunostimulant—such as BCG—induces a response to skin-testing with tuberculin (a soluble preparation of Tubercle bacilli), when tested later. The local reaction is measured at various intervals, for example, 24 hours, 48 hours and 72 hours after injection of tuberculin. Briefly, an immunostimulant (eg. BCG) is used that induces a positive immune response to tuberculin. In the test animal, the tuberculin skin test is preferably carried out on the foot pad. In a predominant Th1 reaction the positive foot pad immune response is usually maximal at 24 hours and diminishes at 48 hours. However, as the Th2 reactivity increases then the 48 hour positive foot pad immune response increases and can even exceed the foot pad immune response at 24 hour. Thus, the assay can be used to assess whether or not the introduction of an immune modulator composition according to the present invention modulates the cellular immune response.

Preferably, the immunostimulant is BCG.

Figure 1:
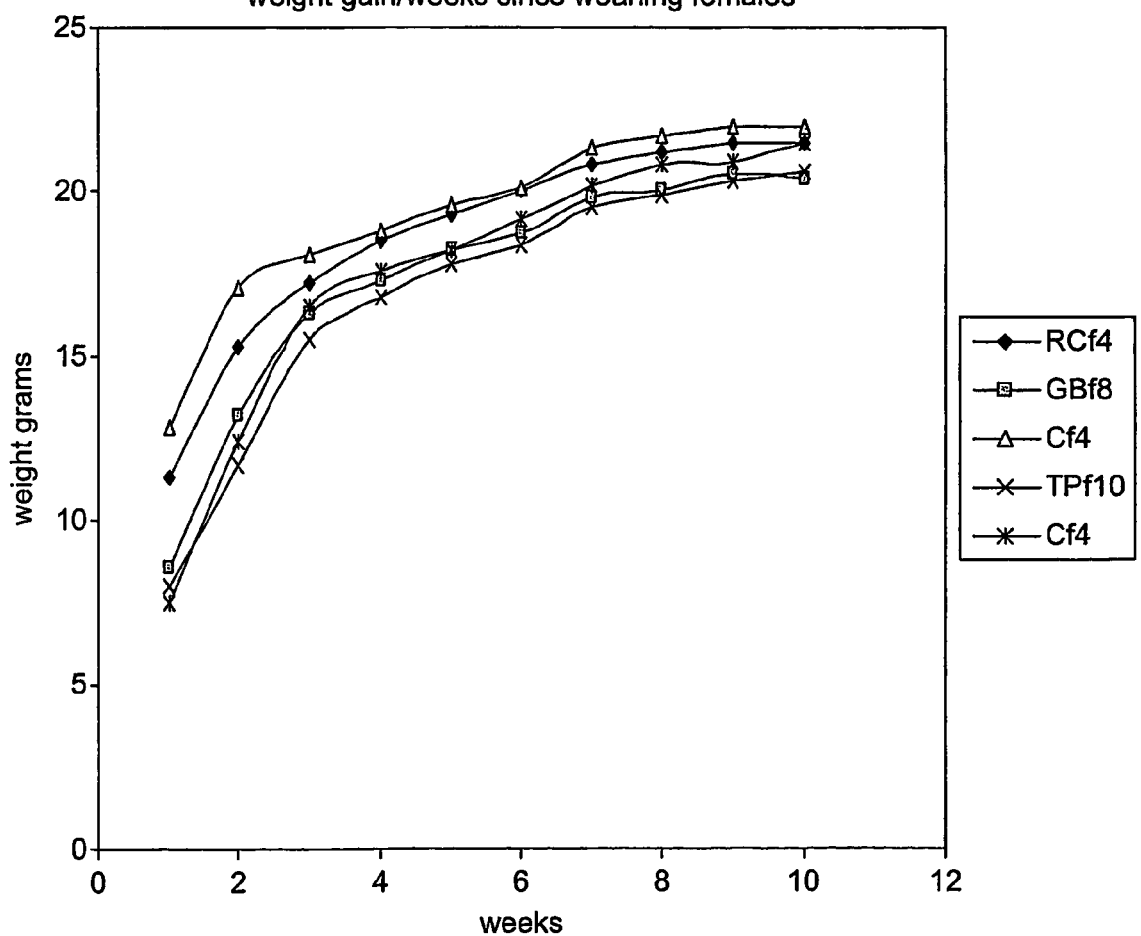
FIG. 1 is a graph demonstrating the results of weight gain means/litter females test and controls over 12 weeks from weaning.
Figure 2:
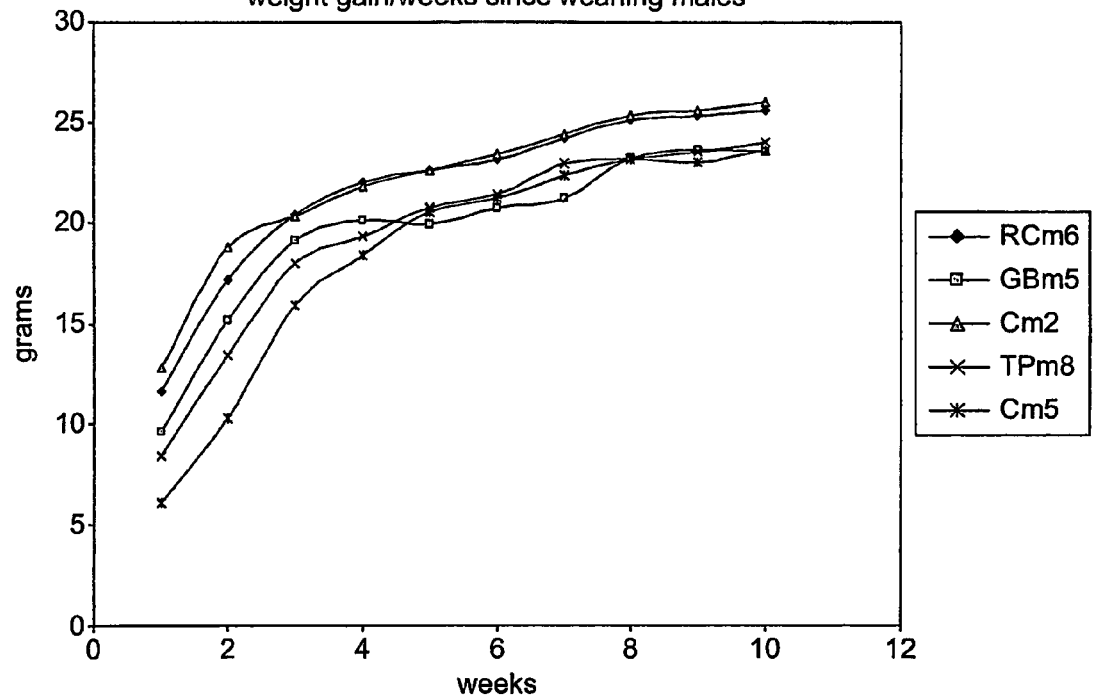
FIG. 2 is a graph demonstrating the results of weight gain mean/litter males test and controls over 12 weeks from weaning.
Figure 3:
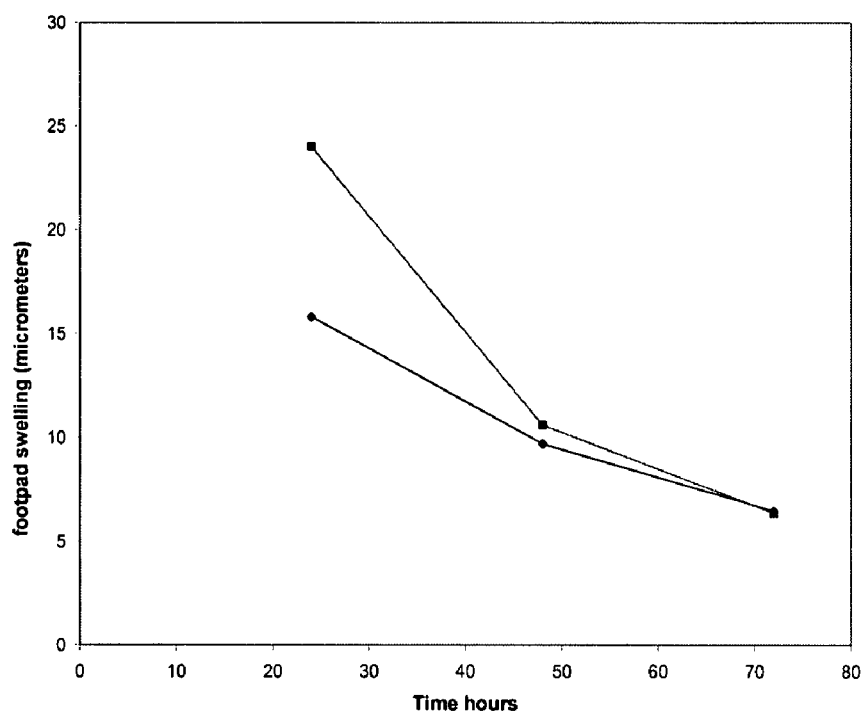
FIG. 3 is a graph demonstrating that *Gordonia bronchialis* enhances the early TH1 effect.
Figure 4:
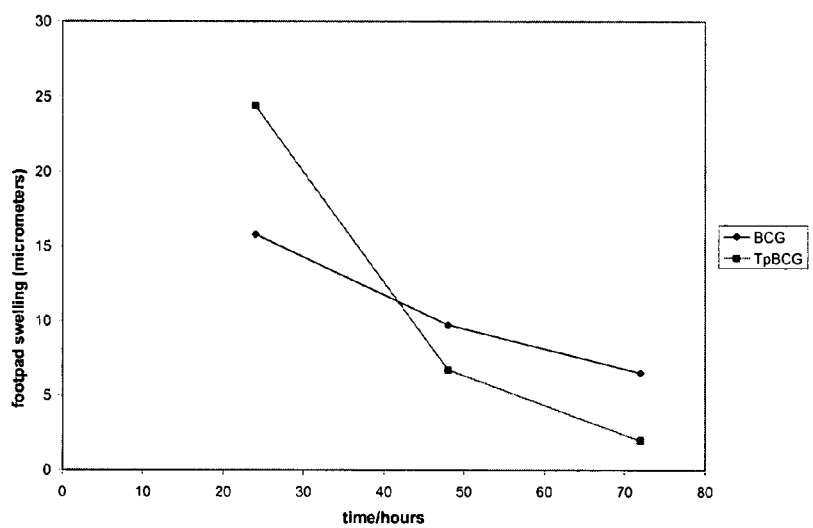
FIG. 4 is a graph demonstrating that *Tsukamurella inchonensis* enhances the early TH1 response and suppresses the late TH2 response

The invention will now be further described by way of Examples, which are meant to serve to assist one of ordinary skill in the art in carrying out the invention and are not intended in any way to limit the scope of the invention.

EXAMPLES

Methods

Tuberculin Skin Test

The tuberculin skin test is an appropriate model assay to assess the effect of an immune modulator composition, i.e. bacterial compositions/suspensions comprising whole killed bacterial cells according to the present invention, on a cellular immune response.

BCG vaccination induces a positive immune response to tuberculin. In mice, the tuberculin skin test is preferably carried out on the foot pad. In a predominant Th1 reaction the positive foot pad immune response is maximal at 24 hours and diminishes at 48 hours. However, as the Th2 reactivity increases then the 48 hour positive foot pad immune response increases and can even exceed the foot pad immune response at 24 hour.

The effect of BCG vaccination is well documented using this tuberculin skin test. Thus, the test assay can be used to assess whether or not the introduction of an immune modulator composition according to the present invention modulates the BCG cellular immune response.

Preparation of a Bacterial Suspension

The bacterial species from the genera *Rhodococcus, Gordonia, Nocardia, Dietzia, Tsukamurella* and *Nocardioides* may be grown in an antigen-free medium, such as Sauton's medium, in a fermenter for 2-28 days. Alternatively, the bacterial species of interest may be grown on a solid slope. Alternative methods would be readily available to those skilled in the art.

The resulting bacterial mass may be harvested and either used directly or after washing to make a suspension in buffer.

The bacterial cell suspension is prepared to contain between 100 nanograms and 10 milligrams bacilli per dose. The bacterial cells are resuspended in water or in a saline. Preferably, the saline is buffered at pH 8.0 with borate. Preferably the bacilli are inactivated (killed), suitably by heating in an autoclave for 15 minutes at 121° C. The resulting bacterial suspension comprises whole cells.

Example 1

Modulation of a Cellular Immune Response by *Rhodococcus ruber* (R.r.)

Group 1: young adult female outbred mice were left unvaccinated as a control group.

Group 2: young adult female outbred mice were vaccinated on day 0 into the scruff of the neck with BCG ($10^5$ bacilli) (Evans).

Group 3: young adult female outbred mice were vaccinated on day 0 into the scruff of the neck with BGC ($10^5$ bacilli) to which heat-killed *Mycobacterium vaccae* (M.v.) ($10^7$ bacilli) had been added.

All mice in Groups 1-3 were foot pad tested for tuberculin immune response at days 10 and 30. Then each mouse was injected with heat-killed *Mycobacterium vaccae* ($10^7$ bacilli) at day 40. At day 50 the tuberculin test on the foot pad was repeated.

Group 4: young adult female outbred mice were left unvaccinated as a further control group.

Group 5: young adult female outbred mice were vaccinated on day 0 into the scruff of the neck with BCG (Evans) ($10^5$ bacilli).

Group 6: young adult female outbred mice were vaccinated on day 0 into the scruff of the neck with BGC ($10^5$ bacilli) to which heat-killed *Mycobacterium vaccae* ($10^7$ bacilli) had been added.

Group 7: young adult female outbred mice were vaccinated on day 0 into the scruff of the neck with BGC ($10^5$ bacilli) to which heat-killed *Rhodococcus ruber* ($10^7$ bacilli) had been added.

Group 8: young adult female outbred mice were vaccinated on day 0 into the scruff of the neck with BCG ($10^5$ bacilli) to which heat-killed *Rhodococcus ruber* ($10^6$ bacilli) had been added.

All mice in Groups 4-7 were foot pad tested for tuberculin immune response at day 30. Then at day 40 each group was divided so that half of each group received no further treatment and the second half of each group received an injection of *Rhodococcus ruber* ($10^7$ bacilli). At day 50 the tuberculin test on the foot pad was repeated. The result of Example 1 are shown in Table 1.

TABLE 1

Modulation of a cellular immune response by *Rhodococcus ruber* (R.r.)

| Day | Tuberculin response at 24 hours | 48 hours | 24-48 difference |
|---|---|---|---|
| Group 1 - control | | | |
| 10 | 6.9 ± 4.5 | 5.3 ± 3.7 | 1.6 |
| 30 | 5.9 ± 4.7 | 5.2 ± 4.5 | 0.7 |
| 50 M.v. | 13.1 ± 5.6 | 14.0 ± 5.2 | +0.9 |
|  | p < 0.01 | p < 0.001 |  |
| Group 2 - BCG | | | |
| 10 | 16.8 ± 11.1 | 16.8 ± 5.5 | 0 |
| 30 | 31.1 ± 17.8 | 16.9 ± 9.1 | 14.2 < 0.05 |
| 50 M.v. | 33.9 ± 12.3 | 19.2 ± 11.3 | 14.7 < 0.02 |
| Group 3- BCG + M.v. | | | |
| 10 | 14.6 ± 8.3 | 9.9 ± 2.7 | 4.7 |
| 30 | 23.8 ± 16.1 | 21.7 ± 11.5 | 2.1 n.s |
| 50 M.v. | 27.4 ± 10.3 | 15.1 ± 5.8 | 12.3 < 0.005 |
| Group 4 - control | | | |
| 30 | 2.8 ± 3.7 | 2.5 ± 2.3 | 0.3 n.s. |
| 50 | 6.4 ± 9.4 | 3.6 ± 7.5 | 2.8 n.s. |
| 50 R.r. | 4.2 ± 5.4 | 1.0 ± 1.7 | 3.2 n.s. |
| Group 5- BCG | | | |
| 30 | 28.8 ± 15.4 | 19.1 ± 10.9 | 9.7 (<0.1) |
| 50 | 33.8 ± 21.6 | 12.0 ± 7.9 | 21.8 (<0.1) |
| 50 R.r. | 40.0 ± 22.4 | 12.2 ± 9.2 | 27.8 < 0.05 |
| Group 6- BCG + M.v. | | | |
| 30 | 19.4 ± 20.5 | 17.7 ± 11.8 | 1.7 n.s. |
| 50 | 56.8 ± 53.8 | 29.4 ± 31.1 | 27.4 n.s. |
| 50 R.r. | 50.0 ± 38.4 | 9.0 ± 10.4 | 41.0 < 0.05 |
| Group 7- BCG + R.r. | | | |
| 30 | 20.6 ± 10.9 | 17.8 ± 10.3 | 2.8 n.s. |
| 50 | 24.8 ± 22.5 | 14.6 ± 13.2 | 10.2 n.s. |
| 50 R.r. | 28.0 ± 13.2 | 11.0 ± 4.7 | 17.0 < 0.05 |
| Group 8 - BCG + R.r./10 group | | | |
| 30 | 19.5 ± 13.9 | 20.9 ± 14.9 | +1.4 |
| 50 R.r. | 37.2 ± 25.2 | 20.2 ± 5.3 | 17.0 n.s. |
| 50 | 26.8 ± 14.8 | 12.8 ± 8.0 | 14.0 (<0.1) |

M.v. = *Mycobacterium vaccae*

In the control Group 1 *Mycobacterium vaccae* treatment induced a statistically significant increase in the immune response to tuberculin after both 24 hours (p<0.01) and 48 hours (p<0.001). However, in the control Group 4, treatment with *Rhodococcus ruber* did not induce a significant change in immune response to tuberculin after both 24 hours and 48 hours. At both time points the M.v. results were significantly greater than the R.r. results (p<0.02).

In the BCG groups (Group 2 and Group 5), the fall in response to tuberculin between 24 hours and 48 hours was greater (p=0.06) in the mice receiving treatment with *Rhodococcus ruber* (the mean fall being 28.2±15.7) than in the mice receiving treatment with *Mycobacterium vaccae* (the mean fall being 14.9±9.6).

In the BCG+*Mycobacterium vaccae* group (Group 3 and Group 6), the fall in response to tuberculin between 24 hours and 48 hours was again greater (p<0.05) in the group receiving treatment with *Rhodococcus ruber* (mean fall being 41.0±41.0) than in mice receiving treatment with *Mycobacterium vaccae* (mean fall being 12.7±7.0).

These data suggest that there is a down-regulation of the Th2 response after treatment with *Rhodococcus ruber*, which is not seen following treatment with *Mycobacterium vaccae*.

In the BCG+R.r. groups (Groups 7 and 8) the effect of adding R.r. $10^7$ (Group 7) or $10^6$ (Group 8) to BCG was very similar and after the second injection with R.r. there was a substantial reduction in response between 24 and 48 hours (15.5±10.0).

Example 2

Modulation of a Cellular Immune Response Using *Nocardia asteroides* (N.a.), *Gordonia bronchialis* (G.b.) or *Tsukamurella inchonensis* (T.p.).

This experiment was designed to compare the effects of foot-pad testing with Tuberculin 28 days after vaccinating groups of 6 mice with BCG alone or with the addition of $10^7$ M.v., R.r., *Nocardia asteroides* (Na.), *Gordonia bronchialis* (G.b.) or *Tsukamurella inchonensis* (T.p.). To find out what the effects were on the immune response to each of these added organisms, the groups of animals were tested in the other foot-pad 28 days after they had been tested with Tuberculin with skin-test reagents made from the organism included in their vaccination (Vaccin, Rubin, Asterin, Bronchialin and Inchonensin).

The results are detailed in Table 2.

TABLE 2

Modulation of a cellular immune response

| Day | Tuberculin response at 24 hours | 48 hours | 24-48 h difference |
|---|---|---|---|
| 1) Control group | | | |
| 28 | 3.8 ± 4.8 | 3.7 ± 3.6 | 0.1 |
| 2) BCG group | | | |
| 28 Tuberculin | 38.0 ± 20.2 | 28.2 ± 17.0 | 9.8 |
| 56 | 65.0 ± 31.2 | 45.8 ± 23.6 | 19.2 |
| 3) BCG + M.v. group | | | |
| 28 Vaccin | 20.3 ± 10.0 | 14.2 ± 5.7 | 6.1 |
| 56 | 18.7 ± 12.1 | 8.0 ± 6.5 | 10.7 |
| 4) BCG + R.r. group | | | |
| 28 Rubin | 31.3 ± 16.0 | 24.2 ± 10.3 | 7.1 |
| 56 | 19.5 ± 7.1 | 12.3 ± 10.4 | 7.2 |
| 5) BCG + N.a. Group | | | |
| 28 Asterin | 24.2 ± 20.8 | 20.2 ± 17.6 | 4.0 |
| 56 | 7.3 ± 8.3 | 5.3 ± 5.0 | 2.0 |
| 6) BCG + G.b. group | | | |
| 28 Bronchialin | 15.8 ± 14.4 | 15.7 ± 13.2 | 0.1 |
| 56 | 11.3 ± 3.4 | 6.2 ± 4.3 | 5.1 |
| 7) BCG + T.p. group | | | |
| 28 Inchonensin | 19.5 ± 7.4 | 15.8 ± 5.7 | 3.7 |
| 56 | 9.8 ± 5.0 | 2.3 ± 2.7 | 7.5 |

All of the bacterial suspensions depressed the 28 day Tuberculin response measured at both 24 and 48 hours, in comparison with that following BCG alone ($p=0.05$; $p=0.2$).

With the exception of Tuberculin and Vaccin, this was the first time that any of these skin test reagents have been used. The differences in responsiveness to the new reagents at 24 hours were probably because they had not been equilibrated except by protein estimation. However, all showed a fall in response between 24 and 48 hours at day 50, suggesting immunoregulatory activity.

Example 3

Local Skin Reactions to Intradermal Injections in Adult Guinea Pigs

The left flank of 3 animals was shaved to give intradermal injections of 0.1 ml containing $10^8$ *M. vaccae* at the head end and 0.1 ml containing $10^9$ *M. vaccae* 5 cm towards the tail end of the animal.

Another 3 animals were shaved in the right flank and given intradermal injections of 0.1 ml containing $10^8$ *R. ruber* at the head end and 0.1 ml containing $10^9$ *R. ruber* 5 cm towards the tail end of the animal.

Diameters of induration in mm.

| Groups | 48 h $10^8$ | 7 d $10^8$ | 14 d $10^8$ | 48 h $10^9$ | 7 d $10^9$ | 14 d $10^9$ |
|---|---|---|---|---|---|---|
| M. vaccae | 2 × 2 | — | — | 4 × 4 | 2 × 3 | — |
| M. vaccae | — | — | — | 2 × 2 | 2 × 2 | 1 × 1 |
| M. vaccae | — | — | — | 5 × 5 | 1 × 2 | — |
| R. ruber | — | — | — | 1 × 1 | 2 × 2 | — |
| R. ruber | — | — | — | 1 × 1 | 2 × 2 | — |
| R. ruber | — | — | — | 2 × 1 | 4 × 3 | 1 × 2 |

In 3 guinea pigs, the local reactions to intradermal injections (the route of injection to be typically used in veterinary and medical practice) of $10^9$ *R. ruber* (a typical dose for human and animal use) were similar to reactions to the same dose of *M. vaccae* in another 3 guinea pigs. At 48 hours after injection, reactions to *R. ruber* were smaller ($p<0.05$) than those to *M. vaccae*. There were no differences at 7 days or 14 days. Thus, *R. ruber* may be even more pharmaceutically acceptable than *M. vaccae*. There are no local reactions to either preparation at the $10^8$ dose.

Example 4

Toxicity Following Subcutaneous Injection

No evidence of toxicity to subcutaneous doses was observed in 17 rats receiving 3 injections of *R. ruber* when they were aged 1 day, 14 days and 28 days.

There were no differences at 7 days or 14 days. Many mice have received injections of various species of the bacteria of the present invention, without any evidence of toxicity.

Example 5

Determination of Bacteria which Enhance Th1 Responses Only

Adjuvant arthritis is the severe experimental arthritis induced in animals by mixtures of oil and mycobacterial extracts (a preparation containing *Mycobacterium butyricum* is particularly effective). It is believed to require a strong Th1 adjuvant to induce this response. The arthritis is regulated by mechanisms down-regulating Th2 (arthritis requires both Th1 and Th2 mechanisms).

Experiment 1

To determine whether *R. ruber* can induce Adjuvant Arthritis.

Three groups of rats aged 60-90 days received in the right hind foot pad:

1. An oil suspension of *M. butyricum* 1 mg/0.1 ml (n=8)
2. An oil suspension of *R. ruber* 1 mg (n=8)
3. An oil and saline emulsion (n=8)

Animals from the first group developed arthritis involving all four limbs, whereas in rats given the oil suspension of *R. ruber*, only the injected foot was affected.

Experiment 2

To determine whether *R. ruber* can induce a Th2 regulatory response in rats following a challenge with *M. butyricum* in oil:—

To test for this, 15 rats were given subcutaneous injections, at different sites, of *R. ruber* $10^7$ in buffered saline on days −42, −28 and −14 before challenge with *M. butyricum* in oily emulsion. A control group of 10 rats were pretreated with physiologic saline following the same schedule and further challenged.

Macroscopic evaluation of Adjuvant Arthritis was performed by visual scoring of individual joints (J Rheumatol 1992; 19:513-5). Each limb was scored 0-4, with the maximum reaching 16 points/rat.

| −42 | −28 | −14 | Day 0 |
|---|---|---|---|
| Rr or saline | Rr or saline | Rr or saline | *M. butyricum* |

Both groups showed no differences in the time of onset of arthritic lesions (usually between 9-11 days after induction), or in the severity of arthritic manifestations. Animals were killed on day 18 for ethical reasons because of disease progression.

Conclusion

These experiments clearly show that *R. ruber* has Th1 adjuvant activity but no Th2 "regulatory" activity. The joint damage in Adjuvant Arthritis is a combined action of Th1 and Th2.

Example 6

Investigating the effects of *Rhodococcus coprophilus* NCIMB 11211, *Gordonia bronchialis* NC10667 and *Tsukamurella inchonensis* NC13040 on Toxicity, in Particular Growth Rate and Subsequent BCG Vaccination in Newborn Mice An alternative test of toxicity is that in which subcutaneous injections of *Gordonia bronchialis, Rhodococcus coprophilus* or *Tsukamurella inchonensis* are given on the day of birth, and again in a separate site, on day 21. These animals, and saline-injected controls were weighed at regular intervals over 3 months.

Methods

9 Late Term Pregnant Balb C Mice are Used.

Preparation of killed bacterial suspension: Suspension prepared from 10 day Sauton antifoam broth culture, centrifuged and resuspended as a 10 mgs/ml in borate buffered saline, autoclaved and stored at 4° C. Dilute 10 mgs/ml, $10^{10}$/ml 1/2 in borate giving $5\times10^9$ and then diluting 1/10 in borate buffer giving a final concentration of $10^7$ in 20μ for use.

Day 1

On day of birth remove newborn mice singly and inject litter with $10^7$ killed suspension into the scruff and return to mother.

Inject control litters with 20 μlitres of M15 borate buffered saline into the scruff.

Litter 1=2 female+3 male (*Rhodococcus coprophilus* NCIMB 11211)

Litter 2=2 female+3 male (*Rhodococcus coprophilus* NCIMB 11211)

Litter 3=5 female+3 male (*Gordonia bronchialis* NC10667)

Litter 4=3 female+4 male (*Gordonia bronchialis* NC10667)

Litter 5=1 female+1 male (Borate buffered saline)

Litter 6=3 female+1 male (Borate buffered saline)

Litter 7=5 female+3 male (*Tsukamurella inchonensis* NC13040)

Litter 8=5 female+4 male (*Tsukamurella inchonensis* NC13040)

Litter 9=4 female+5 male (borate buffered saline)

Day 21

Wean the mice, sex and separate the litters into 2 groups male and female

Weigh and revaccinate. Mark individuals by tail marking with an indelible pen.

Weigh and re tail mark weekly for 3 months.

FIG. 1 demonstrates the results of weight gain means/litter females test and controls over 12 weeks from weaning.

FIG. 2 demonstrates the results of weight gain mean/litter males test and controls over 12 weeks from weaning.

Weight gain is the same in all groups, and only 2/57 animals died over the 3 months. Both were males, that died just after being put together with other males after weaning. Thus it can be concluded that weight gain and progress of the animals was unaffected by the three species tested.

Example 7

The Effect on BCG Immunization Measured Through the Tuberculin Skin Test Response An immune modulator test model is devised, based upon on the principle that vaccination with BCG induces a response to skin-testing with Tuberculin (a soluble preparation of Tubercle bacilli), when tested 4 weeks later. The local reaction is measured 24 hours, 48 hours and 72 hours after injection of Tuberculin. In the mouse, the reaction is usually largest at 24 hours when it is an indicator of the Th1 response to the antigens in Tuberculin. The reaction at 48 hours is usually less and includes a Th2 contribution. The reaction at 72 hours is often little less than at 48 hours and is a Th2 response. This post-BCG Tuberculin reaction can be modulated by prior priming, so that the Th1 and Th2 components of the reaction will reflect the nature of the priming reagent.

Methods

Mice primed according to Example 6 when 3 months old were injected with $10^6$ BCG in 100 μl into the scruff to half of each test and the control group.

At 4 months tuberculin test with reagent T1475 1 mg/ml. Dilute 100 μliters in 1.9 ml to give final concentration of 50 μgms/ml. Store at 4° C. Dose is 2.5 μg in 50 μlitres given into the hind footpad. Tuberculin response swelling as measured using a micrometer at 24, 48 and 72 hours.

Results

FIG. 3 shows that Gordonia bronchialis enhances the 24 hour TH1 effect.

FIG. 4 shows that *Tsukamurella inchonensis* enhances the 24 hour TH1 response and suppresses the 72 hour TH2 response

Figure 5:
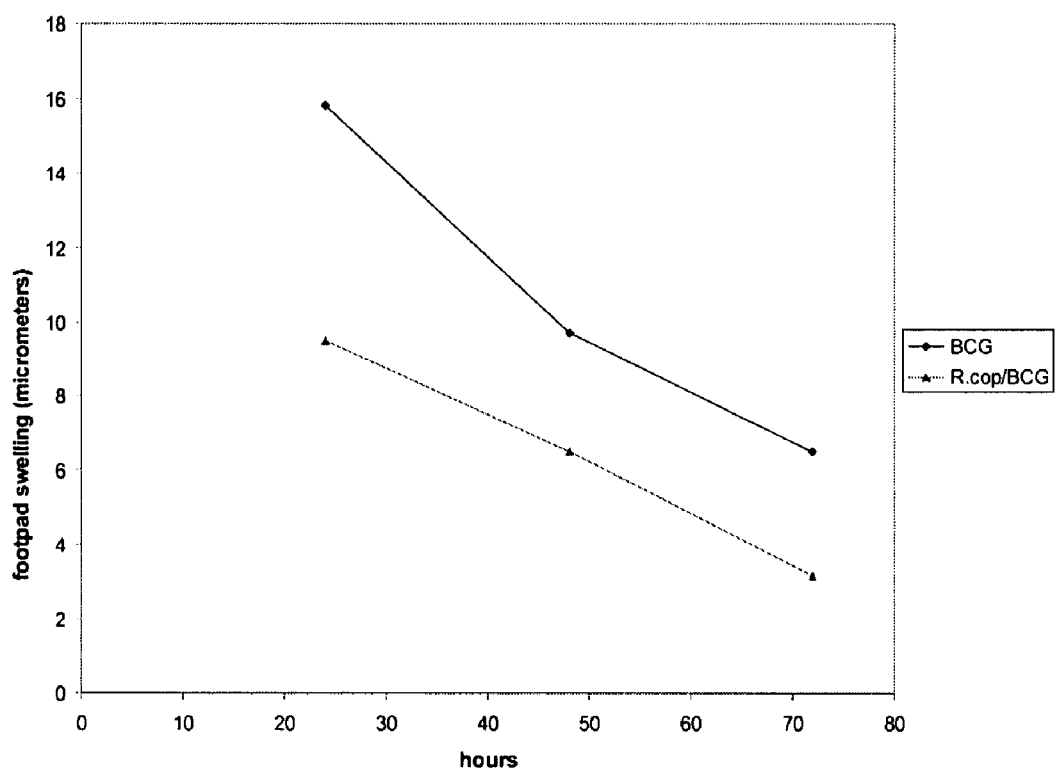
FIG. 5 is a graph demonstrating that *Rhodococcus coprophilus* suppresses both the TH1 and TH2 responses

FIG. 5 shows that *Rhodococcus coprophilus* suppresses both the TH1 and TH2 responses Conclusion The 3 species each induced different effects on the tuberculin test following BCG challenge:

*Gordonia bronchialis* induced an enhanced Th1 response, without changing the Th2 response. *Rhodococcus ruber* also has this function.

*Tsukamurella inchonensis* enhanced the Th1 response and down-regulated the Th2 response.

*Rhodococcus coprophilus* down-regulated both Th1 and Th2 responses.

Given as an adjuvant any of these reagents can modulate the immune response to a subsequent antigen.

These results also clearly show that the influence of 2 priming immunizations with any of the 3 representative species of the invention persists for at least 9 weeks after the second immunization.

Example 8

Immune Modulator Test Model

An immune modulator test model is devised, based upon on the principle that vaccination with BCG induces a response to skin-testing with Tuberculin (a soluble preparation of Tubercle bacilli), when tested 4 weeks later. The local reaction is measured 24 hours, 48 hours and 72 hours after injection of Tuberculin. The reaction is usually largest at 24 hours when it is an indicator of the Th1 response to the antigens in Tuberculin. The reaction at 48 hours is usually less and includes a Th2 contribution. The reaction at 72 hours is often little less than at 48 hours and is a Th2 response. This post-BCG Tuberculin reaction can be modulated by prior priming, so that the Th1 and Th2 components of the reaction will reflect the nature of the priming reagent.

The known immunostimulant, BCG is injected into the scruff of young 3 week old mice and the tuberculin response measured 1 month later by subcutaneous injection of tuberculin into the mouse footpad. The resultant swelling i.e. the "tuberculin response" is then measured at 24, 48 and 72 hours. Swelling at 24 hours is considered an early or Th1 mediated response and swelling at 48 and 72 hours a late or Th2 mediated response. BCG in the healthy mouse stimulates predominantly a Th1 response.

Method (a) BCG Intradermal Vaccine 10 Dose Vial (Evans Medical).

Reconstitute with 1 ml supplied sterile water using a syringe and needle allowing 5 minutes to dissolve. Should be $1 \times 10^7$/ml.

Using a syringe and needle remove all of the vaccine and transfer to a plastic bijou bottle.

Dilute 1/10 0.15 ml in 1.35 ml M15 borate buffered saline gives $10^5$ in 100 μlitres Dose is $10^5$ in 100 μl given into the scruff of the neck.

(b) Tuberculin

T1475 1 mg/ml.

Dilute 100 μl in 1.9 ml to give final concentration of 50 μgms/ml.

Store at 4° C.

Dose is 2.5 μg in 50 μl given intradermally into the hind footpad.

Tuberculin response is measured at 24, 48 and 72 hours using a micrometer

Figure 6:
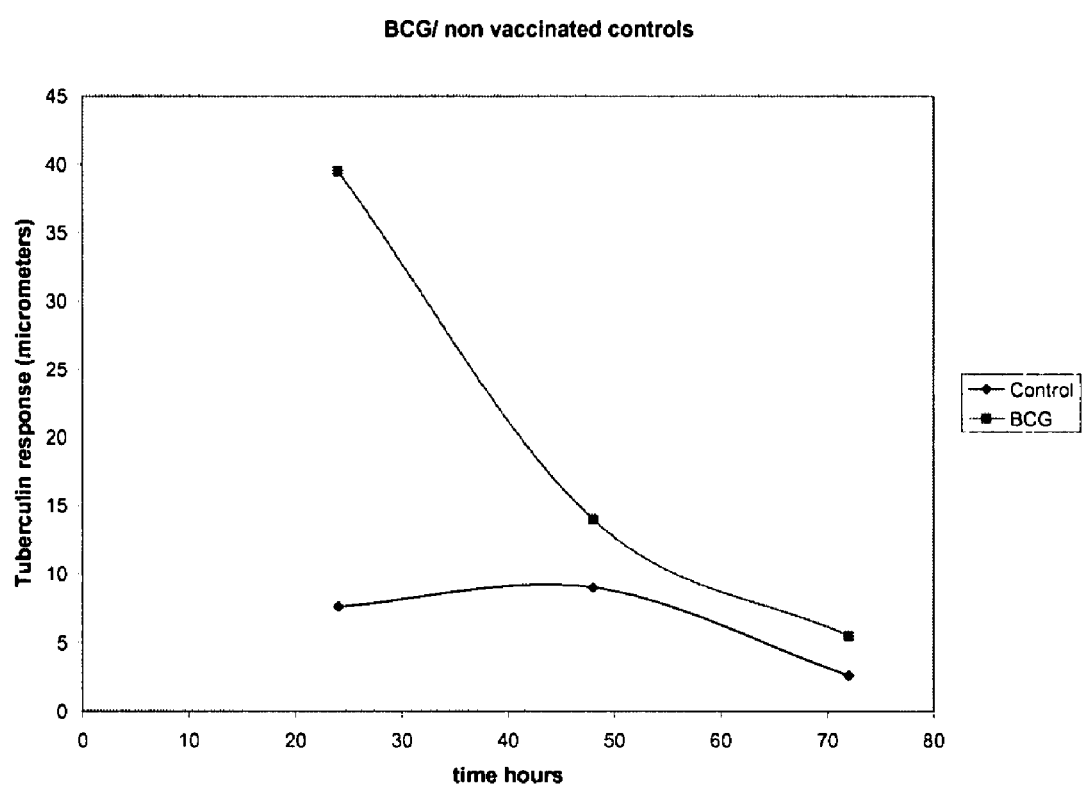
FIG. 6 is a graph demonstrating the tuberculin response to BCG after 1 month compared to non vaccinated controls.

FIG. 6 shows the tuberculin response to BCG after 1 month compared to non vaccinated controls.

(c) Preparation of Test Suspensions

Cultures are grown in Sauton broth harvested by centrifugation and resuspended at a concentration of 10 mg/ml in M15 borate buffered saline and stored at 4° C.

10 mgs/ml=$10^9$ in 100 μl.

Dilute 1/10=$10^8$ in 100 μl.

Add 150 μl $10^8$ to 1.2 ml M15 borate and add 150 μl BCG.

Dose is now $10^5$ BCG+$10^7$ test organism in 100 μl injected into the scruff of the neck.

Results

Figure 7:
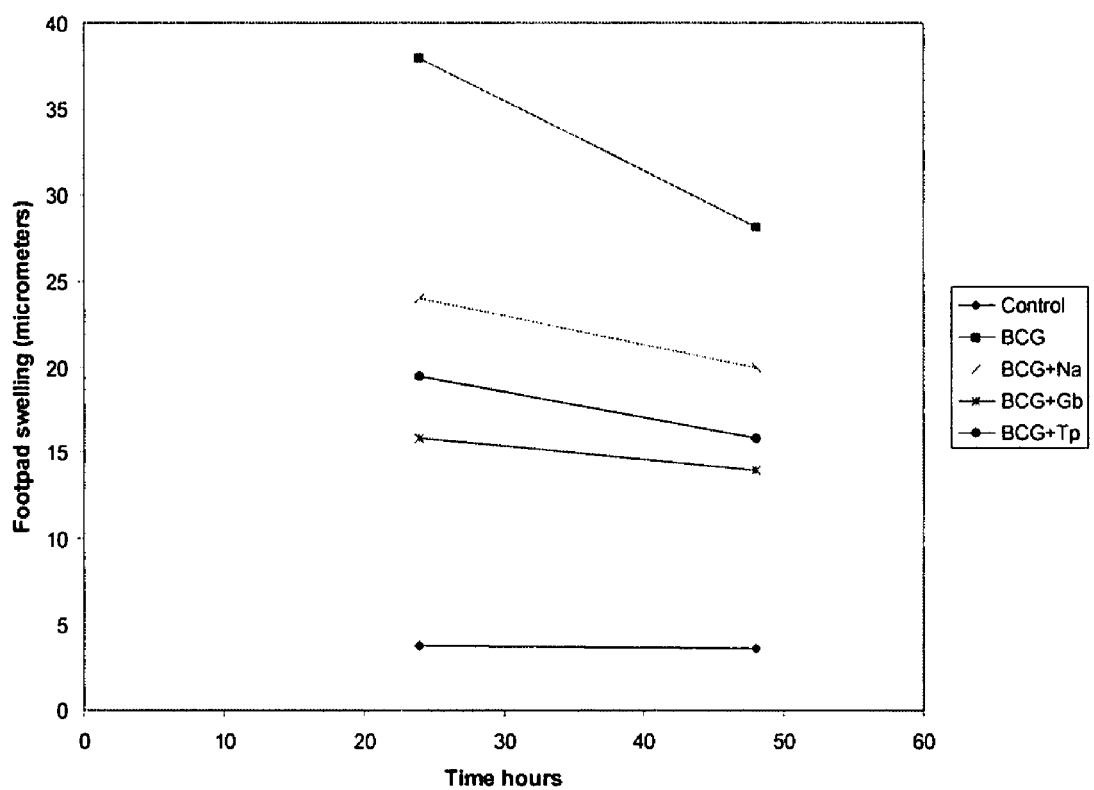
FIG. 7 is a graph demonstrating the immune modulation of the BCG effect by three species of bacteria. Tuberculin responses are measured at 24 and 48 hours. Representative species are (Na) *Nocardia asteroides*; (Gb) *Gordonia bronchialis*; and (Tp) *Tsukamurella inchonensis*.

FIG. 7 is a graph demonstrating the immune modulation of the BCG effect by three species of bacteria. Tuberculin responses are measured at 24 and 48 hours. Representative species are (Na) *Nocardia asteroides*; (Gb) *Gordonia bronchialis*; and (Tp) *Tsukamurella inchonensis*.

Figure 8:
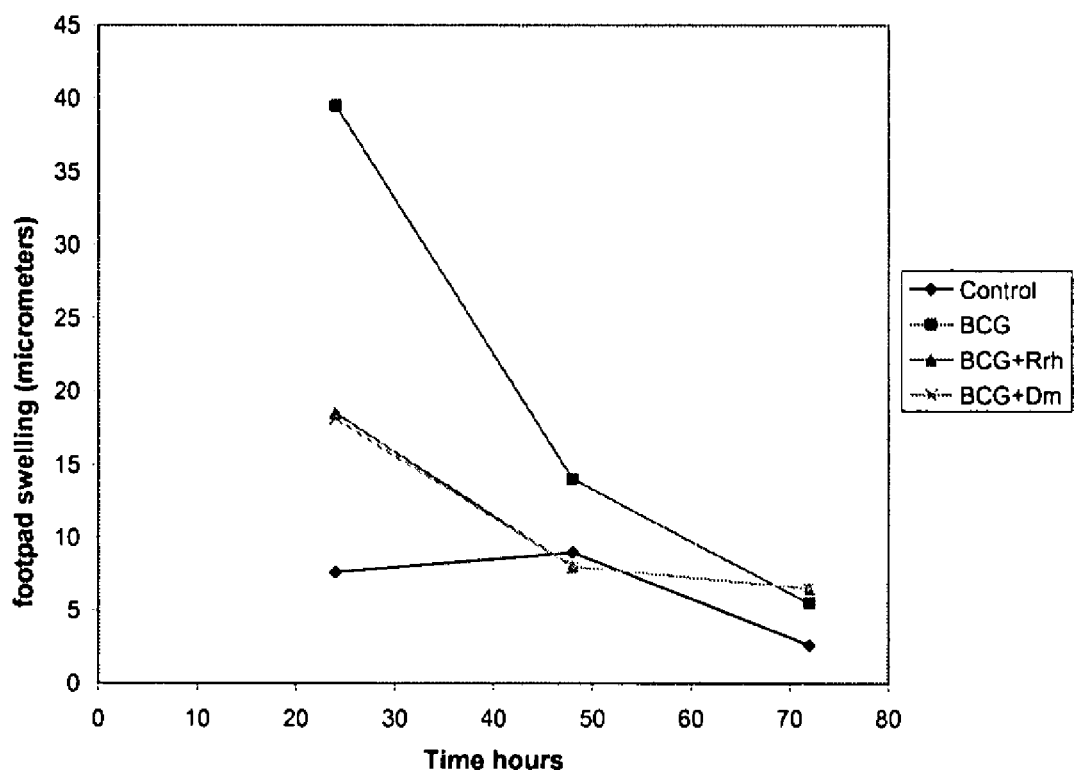
FIG. 8 is a graph demonstrating the immune modulation of BCG/BCG+ by two species of bacteria. Tuberculin responses are measured at 24, 48 and 72 hours. Representative species are (Rrh) *Rhodococcus rhodocrous* and (Dm) *Dietzia maris*.

FIG. 8 is a graph demonstrating the immune modulation of BCG/BCG+ by two species of bacteria. Tuberculin responses are measured at 24, 48 and 72 hours. Representative species are (Rrh) *Rhodococcus rhodocrous* and (Dm) *Dietzia maris*.

Figure 9:
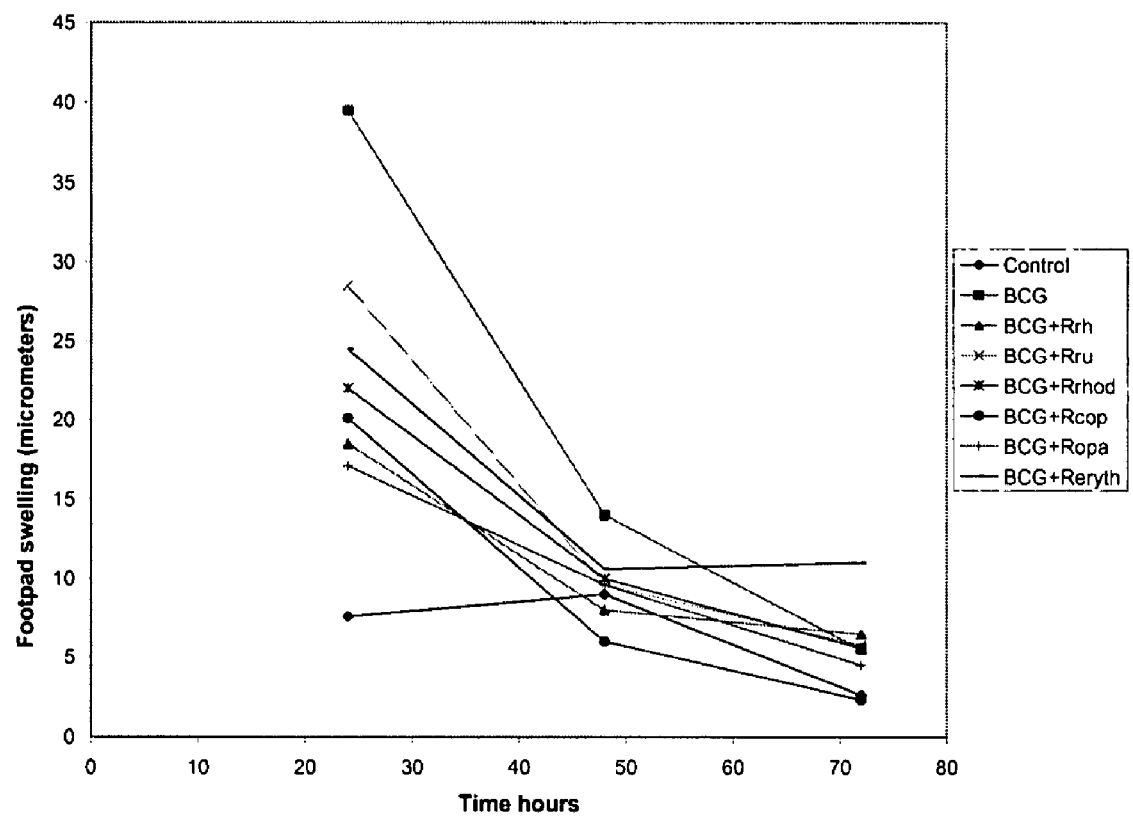
FIG. 9 is a graph demonstrating the immune modulation of the BCG effect by selected species within the genus *Rhodococcus*. Tuberculin responses are measured at 24, 48 and 72 hours. (Rrh) *Rhodococcus rhodocrous*; (Rru) *Rhodococcus ruber*; (Rrhod) *Rhodococcus rhodnii*; (Rcop) *Rhodococcus coprophilus*; (Ropa) *Rhodococcus opacus*; (Reryth) *Rhodococcus erythopolis*.

FIG. 9 is a graph demonstrating the immune modulation of the BCG effect by selected species within the genus *Rhodococcus*. Tuberculin responses are measured at 24, 48 and 72 hours. (Rrh) *Rhodococcus rhodocrous*; (Rru) *Rhodococcus ruber*; (Rrhod) *Rhodococcus rhodnii*; (Rcop) *Rhodococcus coprophilus*; (Ropa) *Rhodococcus opacus*; (Reryth) *Rhodococcus erythopolis*.

Figure 10:
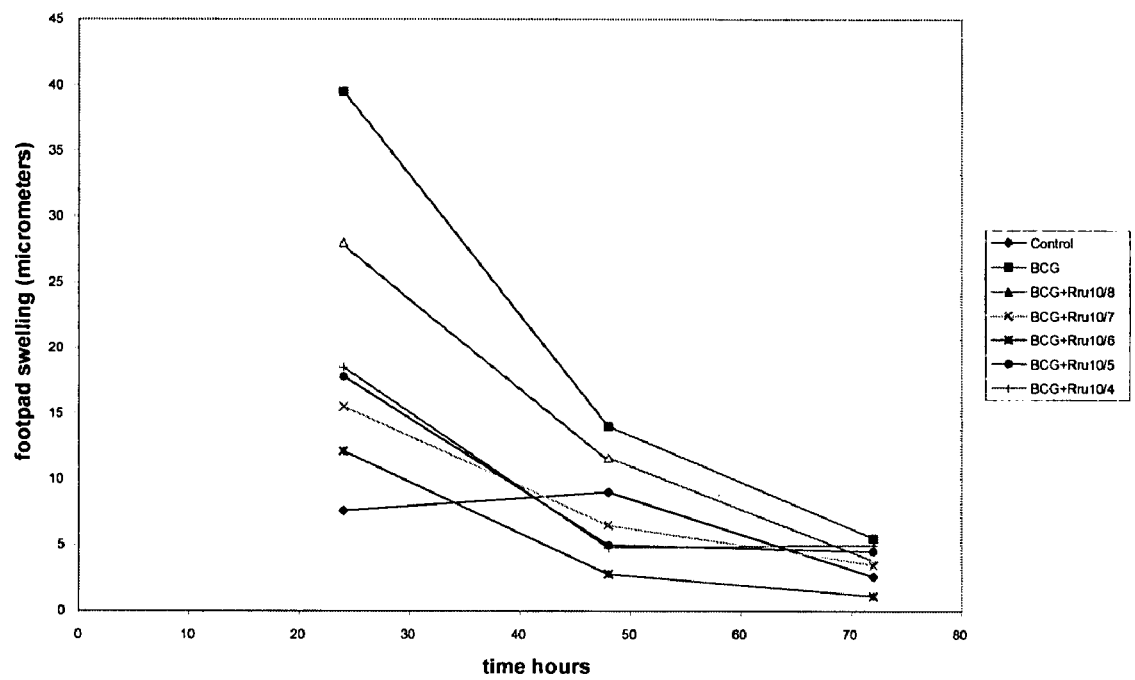
FIG. 10 is a graph demonstrating the optimal dose for *Rhodococcus ruber* using BCG modified with log dilutions of *Rhodococcus ruber* from $10^8$ to $10^4$ compared to BCG alone.

FIG. 10 is a graph demonstrating the optimal dose for *Rhodococcus ruber* using BCG modified with log dilutions of *Rhodococcus ruber* from $10^8$ to $10^4$ compared to BCG alone.

Conclusion

This screening test demonstrates that by mixing test suspensions with BCG and comparing to BCG alone, 28 days later the tuberculin test, as a measure of response to BCG, has been regulated or modified. In this simple model, immunoregulation is shown as a depression in the size of the response at both 24 and 48 hours. This can be further investigated in longer term experiments in which priming with the test suspension is carried out some weeks before challenge with BCG and subsequent Tuberculin testing.

Example 9

To Show that the Suspensions of Whole Cells of the Bacteria are More Effective in Modulating Immunity than Cell Extracts, Comparative Preparations are Made and Tested in a BCG Challenge/Tuberculin Skin Test System 100 mg of *Tsukamurella inchonensis* are suspended in buffered saline (pH8.0) in a pre-weighed centrifuge tube at a concentration of 10 mg wet weight of organisms/ml. The entire 10 ml is treated in an ultrasonicator to break open the majority of organisms (70-80%).

The sonicate is centrifuged at 15000 rpm for an hour in a tube and the supernatant is carefully removed and passed through a 0.2 μm pore-size membrane filter as the test extract. The tube, with deposit, is weighed again to determine the proportion of whole organisms that are not broken open plus cell wall debris etc. This is 64 mg. The volume of extract equivalent to 0.01 mg *T. inchonensis* is then estimated and this is being compared with the equivalent 0.01 mg (approximating to $10^7$) whole bacilli.

Groups of 10 animals are receiving injections of the extract or bacillary whole cell suspensions (equivalent to 0.01 mg/dose) or buffered saline placebo into the scruff of the neck at weaning and 7 days later. Two weeks later animals are challenged with BCG. 28 days later Tuberculin testing is performed with readings taken at 24, 48 and 72 hours.

Results:

Tuberculin responses in mice following BCG vaccination given after priming with nothing, borate buffer, T inchonensis whole cells or soluble antigens (filtered sonicate).

Tuberculin response (micrometer) following BCG given to non-primed animals:—

| No. | 24 hours | 48 hours | 72 hours |
|---|---|---|---|
| 6 | 9 ± 4.2 | 7.7 ± 3.39 | 3.67 ± 3.5 |

Tuberculin response (micrometer) following BCG given to animals primed with borate buffer alone:—

| | | | |
|---|---|---|---|
| 6 | 9 ± 5.7 | 6.3 ± 7.1 | 3.17 ± 2.93 |

Priming with borate buffer has no effect on post-BCG Tuberculin test.

Tuberculin response (micrometer) following BCG given to animals primed with whole heat-killed *T. inchonensis*:—

| | | | |
|---|---|---|---|
| 6 | 7.3 ± 1.03 | 6.17 ± 3.87 | 1.5 ± 2.07 |

Priming with whole *T. inchonensis* decreases Tuberculin responses, notably at 72 hours (Th2 responsiveness).

Tuberculin response (micrometer) following BCG given to animals primed with *T. inchonensis* soluble preparation (filtered sonicate):—

| | | | |
|---|---|---|---|
| 6 | 6.8 ± 6.8 | 11.0 ± 8.0 | 4.6 ± 6.8 |

Priming with *T. inchonensis* filtered sonicate increases responses at 48 hours and 72 hours (Th2 responsiveness). This is probably due to an increase in inflammatory antibody production to shared antigens between BCG and T inchonensis. The results show that priming with sonicate results in a response which is different from that following priming with whole killed organisms.

Preliminary investigations suggest that whole cells of the bacteria are more effective in modulating immunity than cell extracts.

Example 10

Vascular Disease Model—Rat Angioplasty Study

The model is based on an induced reduction of thickening of the intimal layers of the common carotid artery of rats observed following balloon angioplasty.

Experimental groups consisted of 15 male rats each:
Group 1 were rats injected with 0.1 ml of borate-buffered saline at pH 8 subcutaneously (CONTROL)
Group 2 were rats injected with 0.1 ml of borate-buffered saline at pH 8 subcutaneously containing heat-killed environmental saprophytic bacteria Gordonia bronchialis
Group 3 were rats injected with 0.1 ml of borate-buffered saline at pH 8 subcutaneously containing heat-killed environmental saprophytic bacteria *Rhodococcus coprophilus*
Group 4 were rats injected with 0.1 ml of borate-buffered saline at pH 8 subcutaneously containing heat-killed environmental saprophytic bacteria *Tsukamurella inchonensis*
Group 5 were rats injected with 0.1 ml of borate-buffered saline at pH 8 subcutaneously containing heat-killed environmental saprophytic bacteria *Mycobacterium vaccae* (positive control).

Experimental Timeline of Procedures:

All animals were given 7-10 days to accommodate prior to initiation of the experiment on Day 0. They were weighed on Day 0 and at weekly intervals thereafter as a measure of well-being.

Rats in all groups were fed a standard rat chow and allowed free access to water ad libitum.

Day 0 the rats were injected subcutaneously with control or active agent as described above (dose of organism was 50 microgram in 0.1 ml, i.e. 500 micrograms/ml)

Day 21 the rats were injected with a second dose of control/ active agent subcutaneously (dose of organism was 100 micrograms in 0.1 ml, i.e. 1 mg/ml)

Day 49 0.75 ml of blood were taken from the tail vein of each rat and stored in a way appropriate to allow the RNA of cytokines to be measured later.

Day 56 all rats underwent left common carotid artery balloon trauma under anaesthesia.

Day 70 all rats were weighed and euthanased by a Schedule 1 method and the carotid arteries, spleen, left kidney, portion of the left lung, portion of the mid-lobe of the liver, heart and thoracic aorta were taken for histological and immunological analysis. Blood was also taken for further analysis.

Transverse sections of each left carotid artery were cut and stained with haematoxylin and eosin. The muscular and intimal layers were separately measured microscopically and expressed as areas of the cross-section of the vessel. Further sections will be used for immuno-histochemistry to determine immune cell types that are present and the cytokines that are being released.

Blood samples taken on days 49 and 70 were stored in a way suitable for subsequent analyses of the RNA of cytokines, chemokines and other substances relevant to vascular disease.

Results

Figure 11:
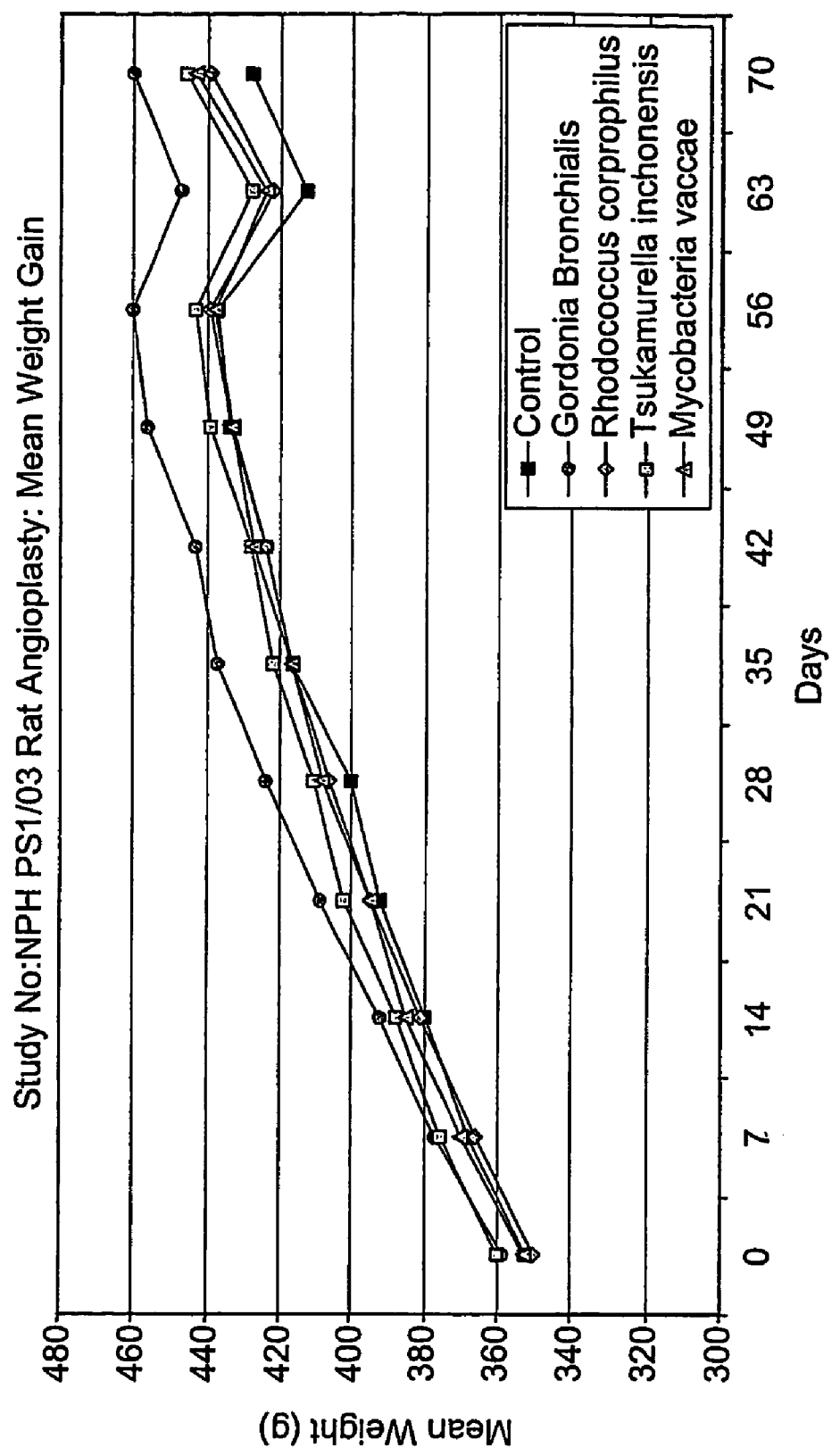
FIG. 11 shows a graph from a rat angioplasty study, which depicts mean rat weight gain following treatment with *Gordonia bronchialis*, *Rhodococcus corprophilus*, or *Tsukamurella inchonensis*, compared with an untreated control and a control treated with *Mycobacteria vaccae*.

The results of rat body weights are shown in the Table below and also in FIG. 11.

TABLE

The weights of rats in gm between Day 0 and Day 70 of Example 10

| Group | 0 | 7 | 14 | 21 | 28 | 35 | 42 | 49 | angioplasty 56 | 63 | 70 |
|---|---|---|---|---|---|---|---|---|---|---|---|
| 1 | 352 | 368 | 380 | 392 | 400 | 417 | 424 | 434 | 437 | 413 | 428 |
| 2 | 359 | 377 | 392 | 409 | 424 | 437 | 443 | 456 | 460 | 447 | 460 |
| 3 | 350 | 366 | 381 | 395 | 406 | 417 | 424 | 433 | 439 | 422 | 439 |
| 4 | 360 | 376 | 388 | 402 | 411 | 422 | 428 | 439 | 443 | 428 | 446 |
| 5 | 353 | 370 | 385 | 395 | 408 | 417 | 427 | 433 | 438 | 424 | 443 |
|   |   |   |   |   |   |   |   |   | 1 v 2 |   | 1 v 2 |
|   |   |   |   |   |   |   |   |   | $p < 0.03$ |   | $p < 0.01$ |

Animals primed with injections of Gordonia bronchialis (2) show a significant weight increase over the placebo group (1) at 2 time points.

Figure 12:
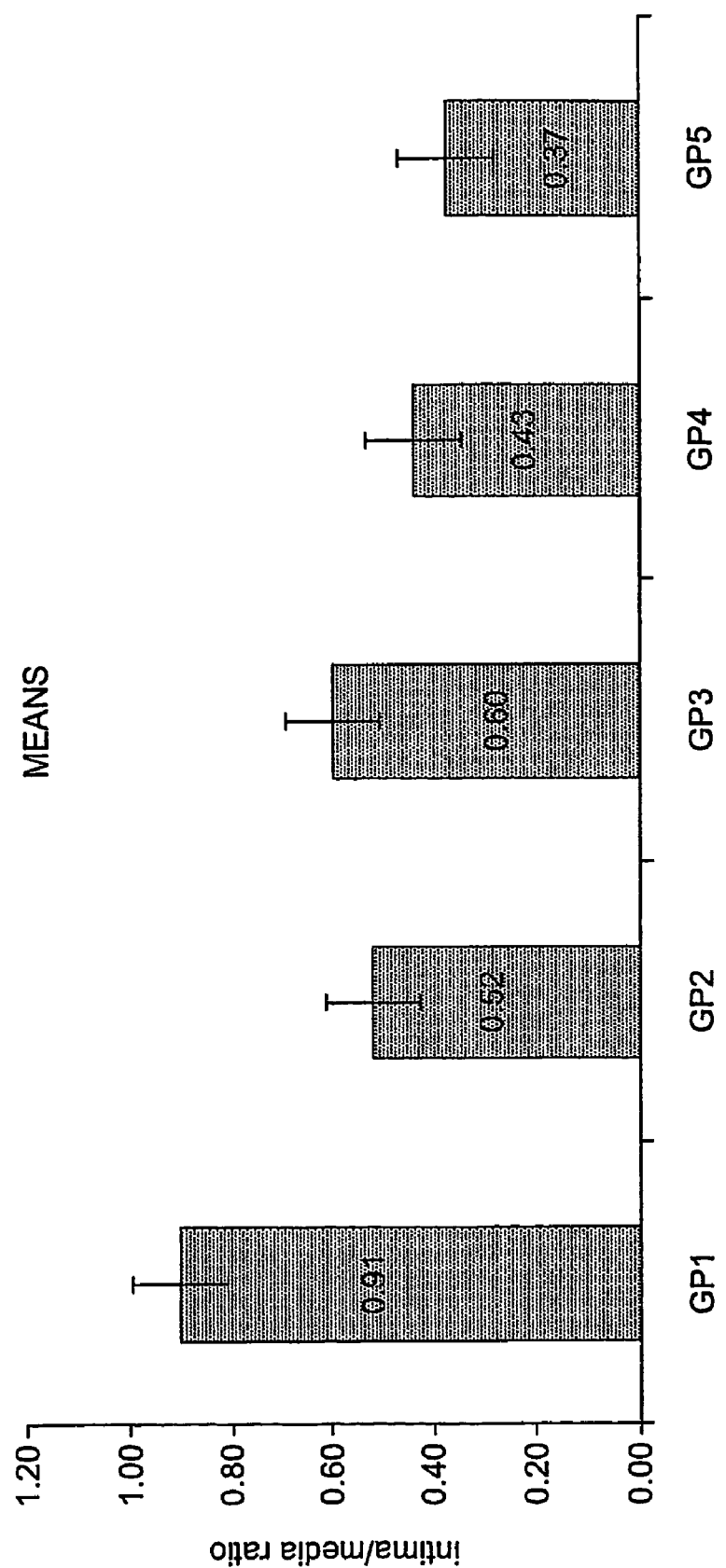
FIG. 12 shows the results for the intima/media thickness ratios in rats following treatment with *Gordonia bronchialis*, *Rhodococcus coprophilus*, or *Tsukamurella inchonensis*, compared with an untreated control and a control treated with *Mycobacteria vaccae*. GP1=Control; GP2=*G. bronchialis*; GP3=*R. coprophilus*; GP4=*T. inchonensis*; GP5=*M. vaccae*).

The results of the measurements of intimal and medial thickness are shown in the Table below and the results for the Intima/media ratios are shown in FIG. 12.

TABLE

The mean values (in pixels) for intima and media in different groups from Example 10.

|  | Intima | Media |  |
|---|---|---|---|
| Placebo | 118233 ± 48506 | 125434 ± 35064 | n = 31* |
| G. bronchialis | 65167 ± 25068 | 131833 ± 39016 | n = 41 |
| R. coprophilus | 89506 ± 35109 | 149469 ± 17913 | n = 34 |
| T. inchonensis | 66153 ± 37546 | 147426 ± 17494 | n = 28 |
| M. vaccae | 50924 ± 27363 | 139523 ± 20206 | n = 38 |

*number of sections studied

Differences from Placebo Values

| G. bronchialis | $p < 0.001$ | n.s. |
| R. coprophilus | $p < 0.01$ | $p < 0.001$ |
| T. inchonensis | $p < 0.001$ | $p < 0.005$ |
| M. vaccae | $p < 0.001$ | $p < 0.05$ |

Highly significant differences are seen between recipients of the active agents and the placebo.

The reduced results for the intima reflect a reduction in post-angioplasty myointimal hyperplasia. This occurs with all four bacterial preparations, most noticeable with *G. bronchialis*, *T. inchonensis* and *M. vaccae*. This effect could make a large contribution to the success of angioplasties.

Medial thickness lost in the placebo group is retained in the active treatment groups, most noticeably after *R. coprophilus* and *T. inchonensis*. The combination of reduced intimal thickness and retained medial thickness, best seen after treatment with *T. inchonensis*, may prove important progress in the potential reduction of chronic graft rejection.

Example 11

Myocarditis in Rats Infected with Trypanosomiasis

Preparation of Animals
i) One day old male "1" rats were injected into the scruff of the neck with $10^7$ *Gordonia bronchialis*, *Rhodococcus ruber*, *Rhodococcus coprophilus*, *Tsukamurella inchonensis* or *Mycobacterium vaccae* in a volume of 0.1 ml via subcutaneous injection. (This was carried out in two experimental rounds, as shown in the table below).
ii) After 14 days, the male "1" rats were given a second subcutaneous injection with $10^7$ of the same organisms in 0.1 ml on the left side.
iii) Animals were challenged with live *Trypanosoma cruzi* on day 21 via the subcutaneous route with $10^6$ trypomastigotes of the Tulahuén strain of *T. cruzi*. Infective blood trypomastigotes were maintained by serial passage in CBi mice.
iv) Bloodstream forms of *T. cruzi* were assessed under standardized conditions, by direct microscopic observation of 5 μl of heparinized tail venous blood, at 7 and 14 days post-infection (pi). Data are expressed as number of parasites/50 fields.
v) 7 days later an additional subcutaneous injection of $10^7$ of the same organism was administered in a volume of 0.1 ml on the right side.

Control animals only received the challenge with *T. cruzi*.
Another group of animals was left unchallenged for comparison purposes.

| | | PARASITEMIAS | | | |
|---|---|---|---|---|---|
| | | Day 7 | | Day 14 | |
| GROUP | n | Mean ± SD | Median (rank) | Mean ± SD | Median (rank) |
| T. cruzi control | 14 | 2.35 ± 1.44 | 2(1-5) | 1.07 ± 1.07 | 1(0-3) |
| M. vaccae | 17 | 1.17 ± 1.01 | 1(0-3) | 1.29 ± 2.1 | 0(0-7) |
| R. ruber | 17 | 0.65 ± 0.78 | 0(1-2) | 0.69 ± 1.01 | 0(0-3) |

$P < 0.01$ for *M. vaccae* and $P = 0.001$ for *R. ruber* compared with the *T. cruzi* control.

Preparation of Animals
One day old male "1" rats were injected into the scruff of the neck with $10^7$ Gordonia bronchialis, *Rhodococcus coprophilus*, or *Tsukamurella inchonensis* in a volume of 0.1 ml via subcutaneous injection. (This was carried out in two experimental rounds, as shown in the table below)

After 14 and 28 days, the male "1" rats were given second and third subcutaneous injections with $10^7$ of the same organisms in 0.1 ml on the left side Animals were challenged with live *Trypanosoma cruzi* on day 21 via the subcutaneous route with $10^6$ trypomastigotes of the Tulahuen strain of *T. cruzi*. Infective blood trypomastigotes were maintained by serial passage in Cbi mice, Control animals only received the challenge with *T. cruzi*
Another group of animals was left for comparison purposes.

|  | | Day 7 | | Day 14 | |
| --- | --- | --- | --- | --- | --- |
| GROUP | n | Mean ± SD | Median (rank) | Mean ± SD | Median (rank) |
| T. cruzi control | 6 | 3.83 ± 4.36 | 4.5 (1-22) | 3.5 ± 2.89 | 2 (0-6) |
| G. bronchiolis | 4 | 3.25 ± 3.3 | 2 (0-8) | 0.33 ± 0.58 | 0.5 (0-5) |
| R. coprophilus | 5 | 1.6 ± 0.89 | 3 (1-8) | 1.0 ± 1.73 | 0 (0-3) |
| T. inchonensis | 6 | 3.83 ± 5.64 | 5 (0-20) | 2.0 ± 1.83 | 2 (0-18) |

P = 0.032 at day 7 and P = 0.05 at day 14 for *R. coprophilus* compared with the *T. cruzi* control (Kruskall-Wallis analysis of variance).

Serum IgG Antibodies Specific to *T. cruzi* 28 Days After Infection with *T. cruzi*.

| Optical Density values from ELISA test | |
| --- | --- |
| T. cruzi control | 0.3 |
| G. bronchialis | 1.4 |
| R. coprophilus | 0.5 |
| T. inchonensis | 0.9 |

CD4+ve Cells in the Myocardium 7, 14 and 21 Days After Challenge with *T. cruzi*.

|  | Day 7 p.i. | Day 14 p.i. | Day 21 p.i. |
| --- | --- | --- | --- |
| T. cruzi control | 26.4 ± 4.5 | 25.6 ± 8.4 | 44.6 ± 10.5 |
| G. bronchialis | 48.6 ± 7.5 | 63.4 ± 8.2 | 74.3 ± 10.8 |
| R. coprophilus | 53.2 ± 9.9 | 50.0 ± 8.1 | 32.9 ± 8.6 |
| T. inchonensis | 40.0 ± 8.5 | 38.6 ± 8.2 | 44.5 ± 9.2 |

The heart muscle of further test subjects will be analysed 3 months after infection with *T. cruzi* for assessment of chronic myocarditis. Preliminary investigations have shown that *Mycobacterium vaccae* has a beneficial effect in reducing chronic myocarditis and it is expected from the above data that some of the test organisms will have beneficial effects in the prevention of chronic myocarditis.

Example 12

Use of *T. inchonensis* to Reduce Post-Coronary-Angioplasty Myointimal Hyperplasia (MIH)

Atherosclerotic vascular disease is the most common cause of death and disability in the world. The development of atherosclerosis is a complex process, with lipid deposition leading to narrowing of arteries and endothelial dysfunction. Evidence is growing that inflammatory responses at the sites of vascular injury play a key role in disposition to atherosclerosis (Schett G, et al J Clin. Invest. 1995, 96: 2569-2477). Rupture of atherosclerotic plaques is the most common cause of sudden arterial occlusion leading to acute ischaemic syndromes such as myocardial infarction, stroke and peripheral artery occlusion. Following an acute ischaemic episode, a number of inflammatory markers are elevated including certain cytokines and C-reactive protein (CRP) (George et al Circ. Res. 2000; 86: 1203-1210; Hansson et al Arteriosclerosis 1989; 9: 567-578; Yokota et al J Intern Med. 1995; 238; 479-489; Ikeda J. Mol. Cell. Cardiol. 1992 Jun. 24 (6): 579-584; Hojo et al Heart 2000 July; 84 (1) 83-7.

Expression of stress proteins, even at the sites of sheer-stress damage to the intima, leads to a local immune response with release of cytokines into the media and intima according to the type of the immune response predominating in the individual at the time (Chan et al Eur J. Vasc. Enodvasc. Surg. 1999 Nov. 18(5):381-5; Mukherjee et al Thromb. Haemost 1996; 75: 258-260; Wright Heart Vessels 2000; 15: 18-22; Sanchez-Margalet et al Clin Chem Lab. Med 2002 August; 40(8); 769-774). Some cytokines lead to thickening of the intima and a change of phenotype in smooth muscle cells of the media, together resulting in myointimal hyperplasia (MIH). Local release of other cytokines results in intimal repair with minimal obstruction of blood flow (Hansson et al Proc. Natl Acac. Sci. USA 1991; 88: 10530-10534; D'Elios et al Transplant Proc 1998; 30: 2373-7; Feldman et al Circulation 2000 Feb. 29; 101 (8): 908-916; Tashiro Coron Artery Dis 2001 March; 12(2): 107-13; Hojo et al Atherosclerosis 2001 May; 156(1): 165-170; Yang et al Circulation 2000 Mar. 7; 101(9); 1019-26; Anguera et al Am. Heart J. 2002 Nov. 144 (5): 811-817; Takase et al Can J. Cardiol. 2003 July; 19(8): 902-906; Tutar et al Circulation 2003 Sep. 30; 108(13):1581-1584 E-pub 2003 Sep. 15; Del Prete et al Blood 1995 Jul. 1; 86(1): 250-257). The purpose of our proposal is to ensure that the latter mechanism is in place.

The link between myointimal hyperplasia (MIH) and inflammation:

Immune mechanisms that lead to the development and maintenance of MIH result in an increase in stress associated with restricted blood flow, the laying down of fatty streaks and the plaques of atherosclerosis. Raised levels of IgG2 antibody to the stress proteins expressed on minimally damaged intimal cells result in local induction of the complement cascade and destruction of the damaged cells (Schett et al (supra); Chan et al (supra); Crisp et al J. Heart Lung Transplant 1994; 81-91; Johnson et al Atherosclerosis 1990; 84: 111-119). Into this site T lymphocytes are attracted that initiate local cytokine production (Hansson 1991 (supra); D'Elios (supra); Mickelson et al J Am Coll Cardiol. 1996 August; 28(2): 345-53). A fatty streak is laid down over the damaged intima beneath which cytokine activity, beneficial or deleterious, takes place that determines repair or atherosclerotic progression. As a non-specific result of local inflammation, the cytokines interleukin (IL)-1 beta and tumour necrosis factor alpha (TNF-$\alpha$) induce IL-6 which in turn potentiates the biosynthesis of acute phase proteins (e.g. fibrinogen, CRP) by hepatocytes (Ikeda et al (supra); Hojo et al (supra); Spaziani et al Ital Heart J. 2002 October: 3(10): 593-597).

MIH can be considered as an exaggerated healing response to vascular injury following a percutaneous coronary intervention (PCI). A cascade of events, which eventually leads to stenosis or occlusion of the vessel, may occur including:

- loss of the basement membrane
- migration of vascular smooth muscle cells (VSMC) from the media into the intima
- VSMC proliferation and phenotypic change to a more secretory fibroblastic cell type
- increased production of extracellular matrix Clinical re-stenosis occurs after percutaneous coronary intervention (PCI) balloon angioplasty and affects approximately 30% of such cases in clinical practice. It is the major cause of failure of such procedures and treatment of the resulting stenosed and blocked vessels/grafts is problematic. The underlying cellular mechanisms leading to MIH are not well understood though thought to be associated with a predominance of helper T cells of type 2 (Th2), producing the cytokines IL-4 and IL-5, in the presence of which TNF-$\alpha$ becomes tissue-damaging (Hernandez-Pando et al Immunology 1994; 82: 591-595). To date no therapy has been developed which can effectively prevent the process. However the role of a locally mediated inflammatory response which may then become a more systemic phenomenon is being accepted as a key part of the failure of PCI. The clinical relevance of the current project relates to the very large numbers of percutaneous coronary interventions that are performed annually in the UK (approximately 40,000) and world-wide. The new generation of drug eluting stents have much lower rates of re-stenosis than "bare metal" stents, but are unlikely to prevent restenosis completely and are expensive. A safe, relatively inexpensive adjunctive therapy to prevent MIH, such as the immunotherapy proposed in this protocol, could have a major clinical impact.

Certain bacterial species possess the ability, when killed, to regulate the immune response to antigens, such as heat-shock proteins, presented with them. Suspensions of such killed bacteria are very safe to use, and the desired immune modulation can be obtained using various species. Recent studies in our laboratory have shown that patients with atherosclerosis may have decreased Th1 immunity as compared to age-matched controls. Thus inflammatory responses to vessel injury is modifiable by altering the pattern of response by appropriate immunotherapy.

There has been much interest in the role that Th1 and Th2 cytokines play in various other human diseases such as tuberculosis, asthma, rheumatoid arthritis and a number of autoimmune conditions (D'Elios M, Del P G. *Transplant Proc* 1998; 30: 2373-7; Shirakawa T, et al. *Science* 1996; 275: 77-79; and Hernandez-Pando R, Rook GAW. *Immunology* 1994; 82: 591-595). Th1 cells produce IFN-$\gamma$, interleukin-2 (IL-2) and TNF. Th2 cells produce IL-4, IL-5, IL-6, IL-10 and IL-13 (Lin E, et al. *Surgery* 2000; 127: 117-126). Both types of T cell can cause cell-mediated inflammation, and both drive antibody formation, though different immunoglobulin subclasses are involved, and the quantity of antibody accompanying a Th2 response is usually much greater. When regulation of Th1 responses fails, Th1-mediated autoimmune diseases such as multiple sclerosis can result (Genain C P, et al. *Science* 1996; 274: 2054-2057). Dysregulated Th2 responses can lead to a variety of pathologies, including allergic reactions, Th-2-mediated autoimmunity and also chronic fibrotic inflammation such as that seen in idiopathic pulmonary fibrosis (IPF) (Wallace W, et al. *Clin. Exp. Immunol.* 1995; 101:436-441; and Du Bois R M. *New Engl. J. Med.* 1999; 341: 1302-1304).

Such TH2 responses to endothelial and vascular smooth muscle cells (VSMC) antigens play a similar causal role in clinical MIH.

In some situations, such as tuberculosis and rheumatoid arthritis, the simultaneous production of Th1 and Th2 cytokines can result in additional tissue damage. At least one mechanism for this is the increased tissue necrotising activity of Th1-associated TNF-$\gamma$ in the presence of the Th2 cytokines IL-4 and IL-5. The part played by such combined activities is uncertain in MIH, but mycobacterial diseases such as tuberculosis and Johne's disease of cattle, in which it occurs, are known to predispose to atherosclerosis (Alibasoglu M, et al. Am J Vet Res. 1962 January; 23:49-57).

Inflammation is now linked to the progression of atherosclerotic vascular disease. Vascular injury, occurring naturally by spontaneous plaque rupture, or by angioplasty, stimulates inflammatory responses that may adversely effect healing and cause myointimal hyperplasia. A preparation derived from a heat-killed bacterium according to the present invention modulates the immune response to vascular injury in patients undergoing percutaneous coronary intervention for symptomatic coronary artery disease. The inflammatory response as measured by venous blood levels of antibodies to stress proteins, a range of cytokines, cortisol, de-hydro epi-androsterone (DHEA) and C-reactive protein will be modified in subjects given the active preparation. A sample size of 50 patients will be sufficient to detect differences of about 20% in the levels of these markers.

Immune Modulation can Affect the Inflammatory Response:

The mode of action of heat-killed T inchonensis is thought to be as a regulator of T-cell maturation in relation to the antigens shared between the bacterial preparation and those of human tissues. Notably these include the 60 and 70 kDa stress proteins of mitochondrial origin known to share some 60% of their amino-acid chain length homology with bacterial 65 and 70 kDa heat-shock-proteins. The regulatory activity of *T. inchonensis* is to depress Th2 mechanisms and enhance Th1 mechanisms, changing the response to intimal expression of stress proteins, and regulating the phenotype of VSMC through local production of cytokines. A predominating Th2 response with high titres of antibodies to stress proteins leads to destruction of intimal cells expressing these proteins by the complement cascade, with local release of type 2 cytokines (IL-4, IL-5 and IL-13), modifying the phenotype of VSMC to one of rapid replication. With a Th1 response, intimal cells expressing stress proteins are thought to be destroyed individually by T cells releasing type I cytokines (IL-2, IFN-$\alpha$, and TNF-$\alpha$) inducing less proliferative phenotypic changes in the VSMC and local tissue repair. The first of these mechanisms would lead to further damage and restenosis, whereas the second should lead to intimal repair without stimulating restenosis.

Such changes in Th cell activity accompany a decrease in plasma cortisol with an increase in plasma DHEA, and effective regulation of inflammation resulting in a return to normal values for C-reactive protein etc.

Although not wishing to be bound by theory, one autoimmune target in the vessel wall may be heat shock protein (HSP) 70.

The mechanisms by which immunotherapy modifies the inflammatory response after vascular injury are not fully understood, but it is thought that the combination of the specific adjuvant activity of *T. inchonensis*, together with antigens shared between the bacilli and the tissues, result in regulation of immunity to that which reduces immune-mediated tissue damage. The endothelial injury caused by angioplasty may be exacerbated by the host immune response to HSP. These HSP in the closely similar form of stress proteins are produced by stressed cells which have been implicated in the pathogenesis and the pathophysiology of various immunological disorders including atherosclerosis (Xu et al Arterioscler. Thromb. 1992; 12: 789-799). It is likely that they will be present on endothelial and smooth muscle cells in the region of an angioplasty. In effect the hsp/stress-protein acts as an auto-antigen, which can then be addressed by the immune system in an appropriate way. This situation can be induced experimentally by immunizing with a cross-reactive mycobacterial hsp (hsp65) which leads to endothelial damage in rabbits and mice. The effect appears to be dependent on IL-4 secreted by Th2 lymphocytes, and is probably mediated by antibody, as described above.

The relevance of these observations from animal studies to man is suggested by the ability of affinity-purified human antibody eluted from hsp65 columns to damage stressed human endothelial cells in vitro (Schett et al (supra)). This finding suggests that the antibody cross-reacts with hsp60, which is the human homologue of hsp65, and may be accessible to antibody when expressed on the membranes of stressed endothelial cells. It has been suggested that such antibodies binding to stressed endothelial cells may be a factor in producing coronary artery disease after heart transplantation (Crisp et al (supra)). Mukherjee et al. showed no association between preoperative antibody levels to hsp65 and coronary restenosis, but did show that those patients where levels of such antibodies dropped after angioplasty were less likely to restenose (Mukherjee et al (supra)). They did not determine the IgG subclass to which the antibodies to hsp 65 belonged, and the reduced levels recorded could have been due to a switch to $IgG_4$ (Th1-associated antibody). In fact the role of antibodies to hsp could be complex, because patients with vascular disease have not only raised antibody, but also raised levels of the hsp/stress-proteins themselves (Wright et al (supra)). Thus an apparent fall in antibody levels may merely reflect an increase in levels of the protein or of antibody binding to the protein. Moreover the hsp/stress-proteins have regulatory effects, and bind to arterial smooth muscle cells, leading to enhanced survival without a requirement for internalization (Johnson et al (supra)).

Pretreatment of patients due to undergo percutaneous coronary intervention with an immunomodulatory reagent prepared from heat-killed *Tsukamurella inchonensis* will down-regulate inflammatory processes, reducing the production of local myointimal hyperplasia and subsequent atheroma formation and re-stenosis of the artery. This will be recognizable by changes in the cytokine content in peripheral blood using the very sensitive "Luminex" method, measuring 22 different cytokines. It will also be detectable through changes in levels of certain stress proteins and of antibodies to them, and through changes in serum cortisol, dehydroepiandrosterone (DHEA), and their derivatives.

To study the effect of injections of a heat killed preparation of *Tsukamurella inchonensis* on (i) inflammatory response, measured by levels of Interferon-γ, TNF-α, IL-6, IL-10, (ii) other measures of T helper cell regulation and function, (iii) levels of circulating stress proteins and the antibodies to them, (iv) C-reactive protein, and (5) plasma levels of cortisol and de-hydro epi-androsterone, observed after elective percutaneous coronary angioplasty (PCI); a randomized double blind controlled parallel group study will be used.

Patients who require PCI for clinical reasons are eligible to take part. The study size is 50 patients who will be randomized to immune therapy with T inchonensis or an inactive vehicle. Patients will receive two injections, 6 weeks and 3 weeks prior to the angioplasty and a third injection 4 weeks after the procedure. Markers of inflammation will be measured prior to the first injection, just prior to the procedure, 24 to 48 hours after the procedure and 6-8 weeks after the procedure. The study will have 2 stages; in the first 10 patients randomized to receive active product or placebo will be investigated by all the mentioned parameters. In the second stage, the remaining patients will be investigated by the methods selected as most appropriate from the first stage.

The first injection will be given intradermally into the upper arm or shoulder area 6 weeks before the scheduled angioplasty and a second injection will be given 3 weeks later. The procedure will be performed 3-5 weeks after the second injection, and a third and final injection will be given 4 weeks after the procedure. The PCI should take place as routinely indicated and there should be a further follow-up at 6-8 weeks which should coincide with the routine clinical appointment. Blood samples for immunological and inflammatory markers should be taken at baseline (prior to the first immune therapy or placebo injection), immediately prior to the PCI procedure, 24-48 hours after the PCI procedure, and 6-8 weeks after the PCI procedure.

Blood sampling protocol: 10-15 ml samples of venous blood will be collected on each of the 4 occasions. These will be for routine haematological and biochemical tests, for a battery of serum cytokine and chemokine assessments, for measurement of levels of circulating stress proteins and the antibodies to them, for the assessment of plasma cortisol and DHEA, for the measurement of inflammatory and vascular disease markers and for storage of RNA for analysis of intracellular cytokine production.

Details of immune therapy preparation: Preparations will be of M/15, borate buffered (pH 8) non-pyrogenic physiological saline (placebo), or of a suspension of heat-killed organisms of the aerobic actinomycete species *Tsukamurella inchonensis*, suspended at 10 mg/ml in the same borate buffer.

The bacilli were grown on a non-antigenic, non-animal-product, liquid medium (approved by the Veterinary Medicines Directorate as free of animal viruses). Incubation was in a shaking waterbath at 32° C. Bacilli were harvested when good growth has been obtained after 10 days of incubation.

The placebo and bacterial suspension were distributed into sterile 2 ml multidose vials, in 0.5±0.1 ml volumes for individual dosage. Vials were autoclaved at 121° C. for 15 minutes in a regularly maintained autoclave with efficacy indicators. After cooling vials were labelled and stored at 4°±1° C. in boxes dedicated to the study.

Randomizing: This will be by production of computer-generated random sequence of number, 1 to 10 and 11 to 60 (to cover patients dropping out or accidents to vials).

Labelling of vials will be with the patient's study number and A, B, or C to indicate whether it is to be used for the first, second or third injection (a peel-off, self-adhesive label will be attached to each vial that can be stuck to the patient's notes against the date administered). Vials of placebo and active product will be similarly labelled and stored in order of use in boxes, following a computer generated randomization scheme.

Administration of the interventions will be by intradermal injection into the skin over alternating deltoid muscles, starting with the left shoulder. The correct vial for the patient will be taken from the refrigerator. Immediately prior to being drawn into a syringe, the vial will be vigorously shaken for about 20 seconds to suspend particulate bacilli. Then 0.1 ml will be withdrawn into a "BD Microfine+ 1 ml U-100 insulin syringe with a 0.33 mm (29 G)×12.7 (fused-in) needle", and immediately administered, care being taken to raise a small area of peau d'orange. The entire dose of 0.1 ml should be injected.

Following injection, the remaining vial with its contents will be returned to a special box in the refrigerator for future checking, if necessary.

Table of procedures

| Procedure/event | Baseline | Time 0 | 3 weeks | 6 weeks + 1-2 days | 10 weeks | 14 weeks |
|---|---|---|---|---|---|---|
| Eligibility check | ✓ | | | | | |
| Consent | ✓ | | | | | |
| Randomisation | | ✓ | | | | |
| History and physical | | ✓ | ✓ | ✓ | ✓ | ✓ |
| Trial intervention | | ✓ | ✓ | | ✓ | |
| Check injection site | | ✓ | ✓ | ✓ | ✓ | ✓ |
| Blood sample | | ✓ | | ✓ ✓ | | ✓ |
| PCI | | | | ✓ | | |
| Adverse event check | | | ✓ | ✓ | ✓ | ✓ |
| Final follow-up | | | | | | ✓ |

Study interventions will be made on 3 occasions, 2 before angioplasty and 1 afterwards. The first 2 should be 21±3 days apart. Angioplasty should follow the second injection by 28-52 days and the third injection of study treatment should be 28±3 days post angioplasty (i.e. 52-80 days after the second injection).

Study Outcomes: The main outcome of interest are serum markers that reflect immune modulation and changes in levels of acute phase reactions as indicators or inflammation. Blood samples will be analysed for a variety of markers but the primary outcome measures of the study will be a comparison of the differences detected between the two treatment groups in the follow-up blood samples in comparison with the baseline samples, and with the sample taken just before PCI.

The following investigations will be carried out on the 10 patients in stage 1 of the study:—

1. Luminex assessment of 22 different cytokines.
2. Plasma cortisol, DHEA and metabolites.
3. Serum levels of the 60/65 kDa and 70 kDa hsp/stress proteins, and the antibodies to them.
4. C-reactive protein levels.
5. Compliment activation.
6. Vascular disease markers.
7. Routine Haematology etc.
8. Pax-gene system studies for intracellular cytokines will be performed if the results of the above tests are inadequate.

The investigations to be performed on the second and larger stage of the trial will be selected from the results obtained from stage 1, as described below:—

The results obtained for the first 10 patients will be analysed by each of the investigators for:

1. Those showing differences between blood samples 1 and 2 (effect of immune modulation).
2. Those showing differences between blood samples 2 and 3 (effect of operative procedure).
3. Those showing differences between blood samples 1 and 4 (long-term effects of treatment and procedure).

The results will then be analyzed according to active or placebo treatment of the patients. Selected investigations showing differences between these 2 groups will be applied to the second, major phase of the study.

Secondary outcomes: Aliquots of the blood samples will be stored for possible later analysis of other vascular inflammatory markers, such as endothelin, von Willibrand's factor etc.

Preliminary investigations suggest that *T. inchonensis* reduces post-coronary-angioplasty myointimal hyperplasia (MIH).

All publications mentioned in the above specification are herein incorporated by reference. Various modifications and variations of the described methods and system of the present invention will be apparent to those skilled in the art without departing from the scope and spirit of the present invention. Although the present invention has been described in connection with specific preferred embodiments, it should be understood that the invention as claimed should not be unduly limited to such specific embodiments. Indeed, various modifications of the described modes for carrying out the invention which are obvious to those skilled in biochemistry and biotechnology or related fields are intended to be within the scope of the following claims.

The invention claimed is:

1. A method for treating an autoimmune disease or an autoimmune disorder comprising administering an effective amount of a composition comprising a whole cell of a bacterium from one or more of the genera *Rhodococcus, Gordonia, Nocardia, Dietzia, Tsukamurella* and *Nocardioides* to a subject wherein said composition modulates a cellular immune response, and wherein the autoimmune disease or autoimmune disorder involves inflammation of the intima of a blood vessel and is a vascular disorder selected from the group consisting of atheroma formation (otherwise known as arteriosclerosis), myointimal hyperplasia (natural or following angioplasty), inflammatory and autoimmune thickening of the intima and/or muscular layer of blood vessels and myocarditis.

2. A method for immune modulation of a subject against an autoimmune disease or an autoimmune disorder comprising administering a composition comprising a whole cell of a bacterium from one or more of the genera *Rhodococcus, Gordonia, Nocardia, Dietzia, Tsukamurella* and *Nocardioides* and wherein the autoimmune disease or autoimmune disorder involves inflammation of the intima of a blood vessel and is a vascular disorder selected from the group consisting of atheroma formation (otherwise known as arteriosclerosis), myointimal hyperplasia (natural or following angioplasty), inflammatory and autoimmune thickening of the intima and/or muscular layer of blood vessels and myocarditis.

3. A method according to claim 1 or claim 2 wherein said bacterium is selected from one or more of the group consisting of *Gordonia bronchialis, Gordonia amarae, Gordonia sputi, Gordonia terrae, Nocardia asteroides, Dietzia maris, Tsukamurella paurometabola, Rhodococcus ruber, Rhodococcus rhodnii, Rhodococcus coprophilus, Rhodococcus opacus, Rhodococcus erythopolis, Nocardioides albus* and *Tsukamurella inchonensis*.

4. A method according to claim 1 or claim 2 wherein said bacterium is killed.

5. The method according to claim 1 or claim 2 wherein said composition is a pharmaceutical composition.

6. The method according to claim 3 wherein said composition is a pharmaceutical composition.

7. The method according to claim 4 wherein said composition is a pharmaceutical composition.

8. The method according to claim 1 or claim 2 wherein said composition is an immune modulator composition.

9. The method according to claim 3 wherein said composition is an immune modulator composition.

10. The method according to claim 4 wherein said composition is an immune modulator composition.

* * * * *